(12) United States Patent
Yang et al.

(10) Patent No.: US 12,380,329 B2
(45) Date of Patent: Aug. 5, 2025

(54) STRUCTURE-BASED DEEP GENERATIVE MODEL FOR BINDING SITE DESCRIPTORS EXTRACTION AND DE NOVO MOLECULAR GENERATION

(71) Applicant: Insilico Medicine IP Limited, Hong Kong (HK)

(72) Inventors: Ya-Chu Yang, Taipei (TW); Tzu-Lan Yeh, Taipei (TW); Yen-Chu Lin, Taipei (TW)

(73) Assignee: INSILICO MEDICINE IP LIMITED, Hong Kong (HK)

( * ) Notice: Subject to any disclaimer, the term of this patent is extended or adjusted under 35 U.S.C. 154(b) by 0 days.

(21) Appl. No.: 18/116,170

(22) Filed: Mar. 1, 2023

(65) Prior Publication Data

US 2023/0281443 A1 Sep. 7, 2023

Related U.S. Application Data

(63) Continuation of application No. PCT/CN2023/078966, filed on Mar. 1, 2023.
(Continued)

(51) Int. Cl.
*G06N 3/08* (2023.01)
*G06F 40/126* (2020.01)
(Continued)

(52) U.S. Cl.
CPC ............ *G06N 3/08* (2013.01); *G06F 40/126* (2020.01); *G06F 40/40* (2020.01); *G06N 3/0442* (2023.01); *G16B 15/00* (2019.02); *G16B 40/20* (2019.02)

(58) Field of Classification Search
CPC ........ G06N 3/08; G06N 3/0442; G16B 15/00; G16B 40/20; G06F 40/126; G06F 40/40
See application file for complete search history.

(56) References Cited

U.S. PATENT DOCUMENTS 10,665,326 B2  5/2020 Aliper et al.
11,049,590 B1 * 6/2021 Lee .......................... G06N 3/08
(Continued)

FOREIGN PATENT DOCUMENTS

CN  111508568 A  8/2020
CN  111614731 A  9/2020
(Continued)

OTHER PUBLICATIONS

Skalic et al. (From Target to Drug: Generative Modeling for the Multimodal Structure-Based Ligand Design, Aug. 2019, pp. 4282-4291) (Year: 2019).*
(Continued)

*Primary Examiner* — George Giroux
(74) *Attorney, Agent, or Firm* — WILSON SONSINI GOODRICH & ROSATI

(57) ABSTRACT

In some aspects, the present disclosure describes a method of sampling a ligand. In some embodiments, the method comprises receiving a target descriptor. In some embodiments, the method comprises generating, in an engineered chemical space, a latent descriptor, based at least in part on the target descriptor. In some embodiments, the method comprises generating a ligand descriptor, based at least in part on the latent descriptor.

22 Claims, 5 Drawing Sheets

Related U.S. Application Data

(60) Provisional application No. 63/315,288, filed on Mar. 1, 2022.

(51) Int. Cl.
*G06F 40/40* (2020.01)
*G06N 3/0442* (2023.01)
*G16B 15/00* (2019.01)
*G16B 40/20* (2019.01)

(56) References Cited

U.S. PATENT DOCUMENTS

| | | | |
|---|---|---|---|
| 11,127,488 B1 | 9/2021 | Bajpai et al. | |
| 11,260,078 B2 | 3/2022 | Aliper et al. | |
| 11,403,521 B2 | 8/2022 | Aliper et al. | |
| 11,450,407 B1* | 9/2022 | Laniado | G16B 15/30 |
| 2007/0198195 A1* | 8/2007 | Shaw | G16C 20/50 |
| | | | 702/22 |
| 2017/0161635 A1 | 6/2017 | Oono et al. | |
| 2017/0193176 A1 | 7/2017 | Borisov et al. | |
| 2017/0277826 A1 | 9/2017 | Ozerov et al. | |
| 2019/0034581 A1 | 1/2019 | Aliper et al. | |
| 2019/0392304 A1* | 12/2019 | Aliper | G16B 40/20 |
| 2020/0082916 A1 | 3/2020 | Polykovskiy et al. | |
| 2020/0090049 A1 | 3/2020 | Aliper et al. | |
| 2020/0286625 A1 | 9/2020 | Aliper et al. | |
| 2020/0342953 A1 | 10/2020 | Morrone et al. | |
| 2021/0057050 A1 | 2/2021 | Zavoronkovs et al. | |
| 2021/0202047 A1 | 7/2021 | Kang et al. | |
| 2021/0233621 A1 | 7/2021 | Zavoronkovs et al. | |
| 2021/0271980 A1 | 9/2021 | Polykovskiy et al. | |
| 2021/0287067 A1 | 9/2021 | Zavoronkovs et al. | |
| 2021/0326660 A1* | 10/2021 | Krishnan | G06N 3/09 |
| 2021/0383898 A1 | 12/2021 | Kuznetsov et al. | |
| 2022/0005552 A1 | 1/2022 | Galkin et al. | |
| 2022/0108766 A1* | 4/2022 | Mackinnon | G16B 40/20 |
| 2022/0172802 A1 | 6/2022 | Konstantinov et al. | |
| 2022/0213429 A1 | 7/2022 | Niebel et al. | |
| 2022/0230712 A1* | 7/2022 | Sheberla | G16C 20/70 |
| 2022/0246233 A1* | 8/2022 | Morrone | G16B 15/30 |
| 2022/0310196 A1 | 9/2022 | Polykovskiy et al. | |
| 2022/0359047 A1* | 11/2022 | Kanazawa | G16C 20/90 |
| 2022/0383992 A1* | 12/2022 | Triendl | G06N 3/045 |
| 2022/0406403 A1* | 12/2022 | Singh | G16B 40/20 |

FOREIGN PATENT DOCUMENTS

| | | |
|---|---|---|
| EP | 1326183 A1 | 7/2003 |
| KR | 20200052450 A | 5/2020 |
| WO | WO-2020234729 A1 | 11/2020 |
| WO | WO-2021038420 A1 | 3/2021 |
| WO | WO-2021165887 A1 | 8/2021 |
| WO | WO-2021229454 A1 | 11/2021 |
| WO | WO-2021240263 A1 | 12/2021 |
| WO | WO-2021243097 A1 | 12/2021 |
| WO | WO-2022058980 A1 | 3/2022 |
| WO | WO-2022259185 A1 | 12/2022 |
| WO | WO-2023165506 A1 | 9/2023 |

OTHER PUBLICATIONS

Mylonas et al. (DeepSurf: a surface-based deep learning approach for the prediction of ligand binding sites on proteins, Jan. 2021, pp. 1681-1690) (Year: 2021).*

Chen et al. (Log Hyperbolic Cosine Loss Improves Variational Auto-Encoder, Sep. 2018, pp. 1-15—listed as Anonymous Authors) (Year: 2018).*

Masuda et al. (Generating 3D Molecular Structures Conditional on a Receptor Binding Site with Deep Generative Models, Nov. 2020, pp. 1-13) (Year: 2020).*

Bjerrum et al. (Improving Chemical Autoencoder Latent Space and Molecular De-novo Generation Diversity with Heteroencoders, Sep. 2018, pp. 1-13) (Year: 2018).*

Hoffmann, et al. Data-driven approach to encoding and decoding 3-d crystal structures. arXiv preprint arXiv:1909.00949 (2019).

Li, et al. Visual semantic reasoning for image-text matching. Published in: 2019 IEEE/CVF International Conference on Computer Vision (ICCV). pp. 4654-4662. Date of Conference: Oct. 27, 2019-Nov. 2, 2019. Conference Location: Seoul, Korea (South).

Shi, et al. Graphsite: Ligand-binding site classification using Deep Graph Neural Network. bioRxiv preprint. https://doi.org/10.1101/2021.12.06.471420; posted Dec. 7, 2021.

Simonovsky, et al. DeeplyTough: Learning Structural Comparison of Protein Binding Sites. J Chem Inf Model. 2020, (60):2356-2366 Publication Date: Feb. 5, 2020 https://doi.org/10.1021/acs.jcim. 9b00554.

Skalic, et al. LigVoxel: inpainting binding pockets using 3D-convolutional neural networks. Bioinformatics. Jan. 15, 2019;35(2):243-250. doi: 10.1093/bioinformatics/bty583.

International search report with written opinion dated May 24, 2023 for PCT/CN2023/078966.

* cited by examiner

STRUCTURE-BASED DEEP GENERATIVE MODEL FOR BINDING SITE DESCRIPTORS EXTRACTION AND DE NOVO MOLECULAR GENERATION

CROSS-REFERENCE

This application is a continuation of International Application No. PCT/CN2023/078966, filed Mar. 1, 2023, which claims the benefit of U.S. Provisional Application No. 63/315,288, filed Mar. 1, 2022, which is incorporated herein by reference in its entirety.

BACKGROUND

Deep generative learning can refer to a method of training a machine learning model to approximate a distribution of a given dataset, while enabling coherent samples to be generated from the data distribution. Machine learning models trained in this way may be referred to as deep generative models.

Deep generative learning can be applied on chemical datasets to create deep generative models for chemistry that allows generation of coherent molecular structures that are not present in a given training dataset of chemical structures.

SUMMARY

In some aspects, the present disclosure describes a method of sampling a ligand, comprising: receiving a target descriptor; generating, in an engineered chemical space, a latent descriptor, based at least in part on the target descriptor; and generating a ligand descriptor, based at least in part on the latent descriptor; wherein the engineered chemical space comprises a unified embedding for at least a plurality of target latent descriptors and a plurality of ligand latent descriptors.

In some embodiments, in the engineered chemical space, a given target latent descriptor of a given target has a similarity with a given ligand latent descriptor of a given ligand when the given ligand targets the given target, and has a dissimilarity when the given ligand does not target the given target.

In some embodiments, the given target latent descriptor is not identical to the given ligand latent descriptor.

In some embodiments, the engineered chemical space is at least partially organized based on spatial information of a plurality of ligands, a plurality of targets, or both.

In some embodiments, the similarity or the dissimilarity is measurable using a similarity function.

In some embodiments, the similarity function comprises a distance-based similarity function, an angle-based similarity function, a set-based similarity function, or any combination thereof.

In some embodiments, the angle-based similarity function is a cosine similarity function.

In some embodiments, the method is performed at least in part by using a neural network.

In some embodiments, the generating in (b) is performed at least in part by using an encoder.

In some embodiments, the generating in (c) is performed at least in part by using a decoder.

In some embodiments, the neural network comprises a bottleneck architecture comprising the encoder and the decoder.

In some embodiments, the bottleneck architecture comprises a U-net.

In some embodiments, the decoder comprises a language model.

In some embodiments, the language model is a long-short-term-memory model (LSTM).

In some embodiments, at least one hidden unit of the LSTM is initialized with the latent descriptor.

In some embodiments, the neural network comprises a convolutional layer.

In some embodiments, the neural network comprises a densely-connected layer.

In some embodiments, the neural network comprises a skip connection.

In some embodiments, the generating the latent descriptor is performed using at least the encoder.

In some embodiments, at least the encoder is trained at least in part by using contrastive learning.

In some embodiments, the contrastive learning is based at least in part on a contrastive loss computed between pairs of target latent descriptors and ligand latent descriptors in a training data.

In some embodiments, the contrastive loss comprises at least: $L(p,f)=[a-sim(p,f)+sim(p,f')]_+ +[a-sim(p,f)+sim(p',f)]_+$, wherein $L(p,f)$ denotes the contrastive loss, a is a margin parameter, p is a first target latent descriptor in a training data, f is a first ligand latent descriptor in the training data, p' is a second target latent descriptor in the training data that is least similar to the first ligand latent descriptor, f' is a second ligand latent descriptor in the training data that is least similar to the first target latent descriptor, sim is a similarity function computed between its parentheticals, and $[x]_+ = \max(x,0)$.

In some embodiments, the generating the ligand descriptor is performed stochastically.

In some embodiments, the language model is trained based at least in part on a first reconstruction loss.

In some embodiments, the first reconstruction loss is a probabilistic loss function.

In some embodiments, the first reconstruction loss comprises at least: $L(X_f, Y_f) = -\Sigma_i^n Y_{f,i} \cdot \log(X_{f,i})$, wherein $L(X_f, Y_f)$ denotes the first reconstruction loss, wherein $-\Sigma_i^n$ denotes a negative summation over each element i of in a total of n elements in the operands, wherein $X_{f,i}$ is a ligand identifier element in the training data, and wherein $Y_{f,i}$ is a ligand identifier element that is reconstructed by the language model.

In some embodiments, the ligand descriptor comprises a ligand identifier.

In some embodiments, the ligand identifier comprises a textual identifier.

In some embodiments, the textual identifier comprises SMILES, InChI, or SELFIES.

In some embodiments, the ligand identifier comprises a molecular adjacency matrix or a molecular graph.

In some embodiments, the bottleneck architecture is trained at least in part on a second reconstruction loss based at least in part on target-ligand interaction.

In some embodiments, the target-ligand interaction is ligand occupancy.

In some embodiments, the second reconstruction loss comprises at least: $L(X_o, Y_o) = \|X_o - Y_o\|_2^2$, wherein $L(X_o, Y_o)$ denotes the second reconstruction loss, wherein $X_o$ is a ligand occupancy descriptor in the training data, and wherein $Y_o$ is a reconstruction of the ligand occupancy descriptor by the autoencoder.

In some embodiments, the target descriptor comprises a protein target descriptor.

In some embodiments, the target descriptor comprises a protein pocket descriptor.

In some embodiments, the target descriptor comprises features that describe at least one of: hydrophobicity, aromaticity, hydrogen bond accepting, hydrogen bond donating, positive ionizability, negative ionizability, metallicity, pocket occupancy, hydrogen bond interaction ability, hydrophobic interaction ability, pi-pi interaction ability, and halogen interaction ability.

In some embodiments, the protein pocket descriptor comprises a spatial map of one or more protein targets.

In some embodiments, the spatial map is a grid.

In some embodiments, the spatial map is a rectangular grid.

In some embodiments, the spatial map comprises at least 3 dimensions.

In some embodiments, the spatial map comprises a resolution less than about 3.5 Angstroms.

In some aspects, the present disclosure describes a method of machine learning an engineered chemical space, comprising: providing a neural network comprising: an input layer configured to receive at least a target descriptor; a latent layer configured to output at least a latent descriptor, wherein the latent layer is connected to the input layer; an output layer configured to output at least a target-ligand interaction descriptor, wherein the output layer is connected to the latent layer; at least one parameter; providing training data comprising a plurality of target descriptors, a plurality of target-ligand interaction descriptors, and a plurality of ligand latent descriptors; training the neural network, by (i) inputting at least the plurality of target descriptors at the input layer of the neural network, (ii) outputting a plurality of output latent descriptors at the latent layer and a plurality of output target-ligand interaction descriptors at the output layer, and (iii) optimizing a plurality of loss functions based at least in part on the plurality of output latent descriptors and the plurality of output target-ligand interaction descriptors, by updating the at least one parameter of the neural network, such that the neural network learns the engineered chemical space comprising a unified embedding for at least the plurality of target descriptors and the plurality of ligand latent descriptors.

In some embodiments, the engineered chemical space is at least partially organized based on spatial information of the plurality of target descriptors and the plurality of ligand latent descriptors.

In some embodiments, in the engineered chemical space, a given target latent descriptor of a given target has a similarity with a given ligand latent descriptor of a given ligand when the given ligand targets the given target, and has a dissimilarity when the given ligand does not target the given target.

In some embodiments, the given target latent descriptor is not identical to the given ligand latent descriptor.

In some embodiments, the similarity or the dissimilarity is measurable using a similarity function.

In some embodiments, the plurality of loss functions comprises a contrastive loss function computed between a plurality of pairs formed between a plurality of target latent descriptors output by the latent layer and the plurality ligand latent descriptors.

In some embodiments, the training the neural network comprises optimizing a loss function comprising a first reconstruction loss function computed between the plurality of target-ligand interaction descriptors of the training data and a plurality of reconstructed target-ligand interaction descriptors output by the first output layer.

In some embodiments, the neural network further comprises a second output layer configured to output at least a ligand descriptor, wherein the second output layer is connected to the latent layer.

In some embodiments, the training data further comprises a plurality of ligand descriptors.

In some embodiments, the training the neural network further comprises outputting a plurality of output ligand descriptors, and optimizing a loss function comprising a second reconstruction loss function computed between the plurality of ligand descriptors of the training data and a plurality of output target-ligand interaction descriptors output by the second output layer.

In some embodiments, the plurality of target descriptors of the training data comprises features that describe at least one of: hydrophobicity, aromaticity, hydrogen bond accepting, hydrogen bond donating, positive ionizability, negative ionizability, metallicity, pocket occupancy, hydrogen bond interaction ability, hydrophobic interaction ability, pi-pi interaction ability, and halogen interaction ability.

In some embodiments, the plurality of target-ligand interaction descriptors in the training data comprises ligand occupancy of a given target.

In some embodiments, the plurality of ligand latent descriptors in the training data comprises SMILES of a given ligand.

In some embodiments, the neural network further comprises a plurality of hidden layers connecting at least two of: the input layer, the latent layer, and first output layer, and the second output layer.

In some aspects, the present disclosure describes a computer-implemented method, implementing any one of the methods disclosed herein using in a computer.

In some aspects, the present disclosure describes a computer program product comprising a computer-readable medium having computer-executable code encoded therein, the computer-executable code adapted to be executed to implement any one of the methods disclosed herein.

In some aspects, the present disclosure describes a non-transitory computer-readable storage media encoded with a computer program including instructions executable by one or more processors to implement any one of the methods disclosed herein.

In some aspects, the present disclosure describes a computer-implemented system comprising: a digital processing device comprising: at least one processor, an operating system configured to perform executable instructions, a memory, and a computer program including instructions executable by the digital processing device to implement any one of the methods disclosed herein.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

BRIEF DESCRIPTION OF THE DRAWINGS

The novel features of the disclosure are set forth with particularity in the appended claims. A better understanding of the features and advantages of the present disclosure will be obtained by reference to the following detailed description that sets forth illustrative embodiments, in which the principles of the disclosure are utilized, and the accompanying drawings of which:

DETAILED DESCRIPTION

Figure 1:
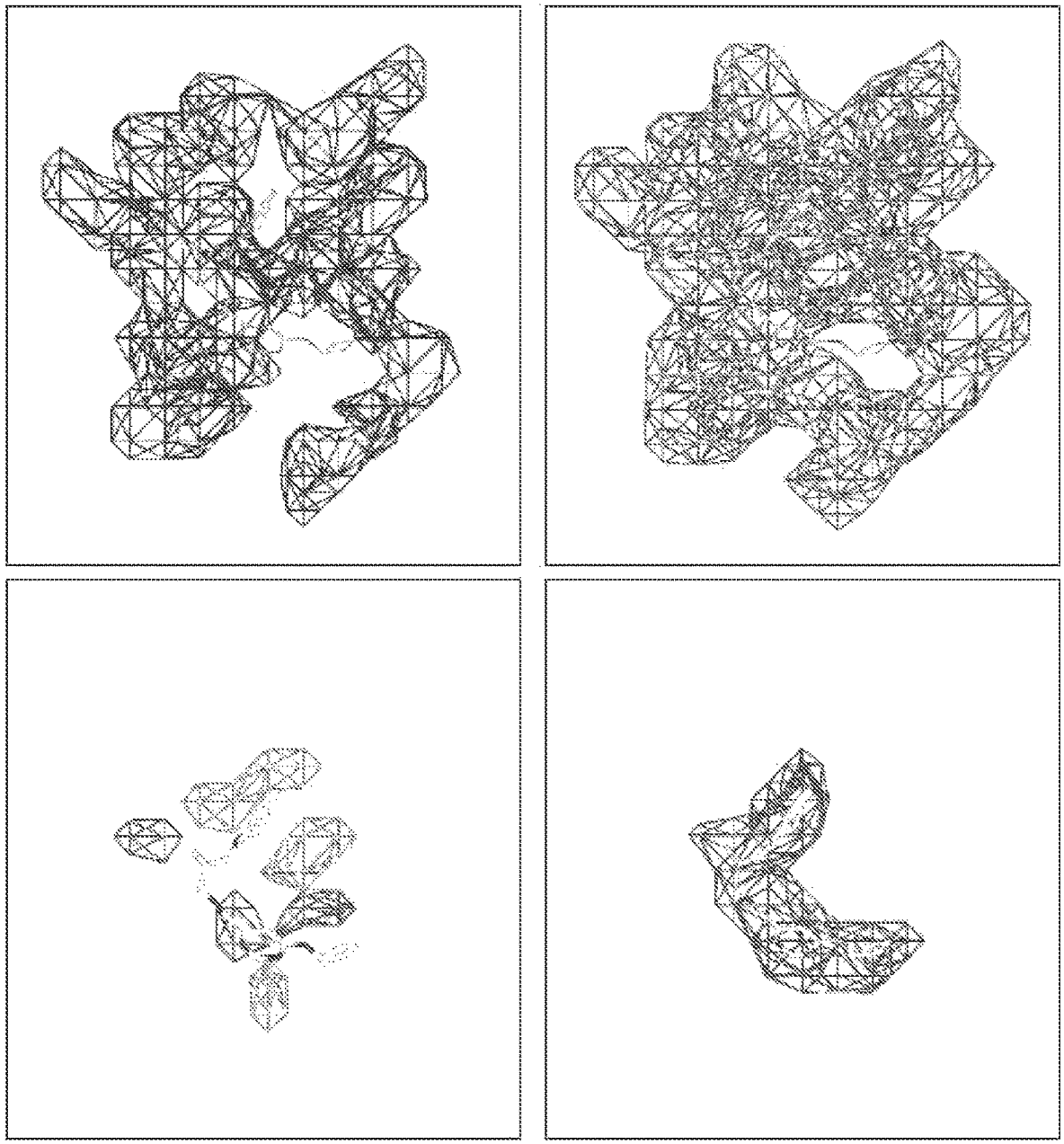
FIG. 1 illustrates pharmacophore property channels of a dataset, in accordance with some embodiments. A protein-ligand pair is represented as 4D tensor having 13 pharmacophore property channels: 'hydrophobic', 'aromatic', 'hbond_acceptor', 'hbond_donor', 'positive_ionizable', 'negative_ionizable', 'metal', 'pocket occupancies', 'residue hbond interaction', 'residue hydrophobic interaction', 'residue pi-pi interaction', 'residue halogen interaction', and 'ligand occupancies'. The top left panel illustrates channel 1 ('hydrophobic'). The top right panel illustrates channel 8 ('pocket occupancies'). The bottom left panel illustrates channel 9 ('residue hbond interaction') in gray and channel 10 ('residue hydrophobic interaction') in white. The bottom right panel illustrates channel 13 ('ligand occupancies').

Deep generative learning can be applied on chemical datasets to create deep generative models for chemistry (herein may synonymously be referred to as generative chemical models) that allow generation of coherent chemical descriptors that are not present in a given training chemical dataset. Generative chemical models can be used to access latent information contained in chemical datasets to provide chemical descriptors that correspond to substances having a specific set of properties or a specific set of purposes. For example, a SMILES identifier for a drug targeting a specific protein may be generated. In another example, a chemical formula for a material having a proper set of properties for an industrial application may be generated.

A consideration in creating generative chemical models involves designing an engineered chemical space (which may herein be synonymously referred to as a latent space). Some machine learning models involve employing a technique to compress information supported in high dimensional space to low dimensional space. A simple example of the technique involves training a neural network comprising a bottleneck layer to autoencode a chemical structure, wherein the bottleneck layer has lower number of dimensions than either the input or the output of the neural network.

In some aspects, the present disclosure describes systems and methods for designing an engineered chemical space in a multi-task learning framework. The systems and methods of the present disclosure can be useful when incorporating at least two sources of chemical information into one unified embedding space. The at least two sources of chemical information may be embedded such that they both comprise a similar embedding manifold, however, the individual embedding points for a given dataset may be embedded on different coordinates. For example, embeddings for protein targets and ligands that occupy the protein targets may be embedded, such that corresponding protein and ligand pairs are embedded in proximity but not necessarily at identical coordinates in an embedding space. Therefore, an embedding for a protein pocket may be proximal to a plurality of embeddings for ligands that may target the protein pocket; and an embedding for a ligand may be proximal to a plurality of protein pockets that the ligand may target. The engineered chemical space may be constructed such that the large-scale structure (e.g., a topology) of the protein pocket embeddings and the ligand embeddings may be similar but not identical. In some embodiments, this is achieved by using a contrastive learning method.

The systems and methods of the present disclosure can be useful when training at least two tasks to a neural network, when one task may be partially related to another. For example, a task for generating a spatial grid of a ligand occupying a protein pocket may be partially related to a task for generating a SMILES string of the ligand. Information relevant for generating the spatial grid may contain more information than it is necessary for generating an identifier of the ligand, and vice versa. A neural network may be constructed such that information relevant for generating the spatial grid is partially incorporated into generating the SMILES string. A neural network may be constructed such that information relevant for generating the SMILES string is partially incorporated into generating the spatial grid. Further, the engineered chemical space may be constructed such that it comprises both spatial representations (e.g., protein pocket occupancy by a ligand) and textual representations (e.g., ligand SMILES). In some embodiments, this may be achieved by using a U-net neural network.

Engineered Chemical Space

In some embodiments, the engineered chemical space may be formed using dimensionality reduction. The terms reducing, dimensionality reduction, projection, component analysis, feature space reduction, latent space engineering, feature space engineering, representation engineering, or latent space embedding can refer to a method of transforming a given data with an initial number of dimensions to another form of data that has fewer dimensions than the initial number of dimensions. In some embodiments, the terms can refer to the principle of reducing a set of input dimensions to a smaller set of output dimensions.

In some embodiments, the engineered chemical space comprises a unified embedding for at least a plurality of target descriptors and a plurality of ligand descriptors. In some embodiments, the engineered chemical space is trained using contrastive learning to create the unified embedding for at least the plurality of target descriptors and the plurality of ligand descriptors. In some embodiments, in the engineered chemical space, a given target latent descriptor of a given target has a similarity with a given ligand latent descriptor of a given ligand when the given ligand targets the given target, and has a dissimilarity when the given ligand does not target the given target. In some embodiments, the engineered chemical space is at least partially organized based on spatial information of a plurality of ligands, a plurality of targets, or both. In some embodiments, the given target latent descriptor is not identical to the given ligand latent descriptor.

In some embodiments, the similarity or the dissimilarity is measurable using a similarity function. In some embodiments, the similarity function comprises a distance-based similarity function, an angle-based similarity function, a set-based similarity function, or any combination thereof. In some embodiments, the angle-based similarity function is a cosine similarity function. In some embodiments, the distance-based similarity function may be based at least in part on a Euclidean distance. In some embodiments, the set-based similarity function may be a clustering function.

In some embodiments, in the engineered chemical space, a plurality of given ligand latent descriptors for a plurality of given ligands may form a distinct cluster or be in proximity with one another when the plurality of given ligands target a given target or a set of similar targets. In some embodiments, in the engineered chemical space, a plurality of given target latent descriptors for a plurality of given targets may form a distinct cluster or be in proximity with one another when the plurality of targets are targetable by a given ligand or a set of similar ligands.

In some embodiments, the embedding for a plurality of target descriptors is a transformation of data in one representation to another representation. In some embodiments, the embedding for a plurality of ligand descriptors is a transformation of data in one representation to another representation. In some embodiments, the transformation may be transforming a form of data into another form of data with less dimensions. In some embodiments, the transformation can comprise at least partially linearizing one or more curved paths in the data in a high dimensional space. In some embodiments, the transformation can be performed on data comprising data in Euclidean space. In some embodiments, the transformation can be performed on data comprising data in graph space. In some embodiments, the transformation can be performed on data in a discrete space. In some embodiments, the transformation can be performed on data comprising data in frequency space. In some embodiments, the transformation can transform data in discrete space to continuous space, continuous space to discrete space, graph space to continuous space, continuous space to graph space, graph space to discrete space, discrete space to graph space, or any combination thereof. In some embodiments, the transformation can comprise transforming data in discrete space into a frequency domain. In some embodiments, the transformation can comprise transforming data in continuous space into a frequency domain. In some embodiments, the transformation can comprise transforming data in graph space into a frequency domain.

In some embodiments, a method or system of the present disclosure may use clustering. The terms clustering or cluster analysis can refer to a method of grouping samples in a dataset by some measure. Samples can be grouped in a set space, for example, element 'a' is in set 'A'. Samples can be grouped in a continuous space, for example, element 'a' is a point in Euclidean space within a distance '1' away from a centroid of the elements comprising cluster 'A'. Samples can be grouped in a graph space, for example, element 'a' is highly connected to elements comprising cluster 'A'. These terms can refer to the principle of organizing a plurality of elements into groups in some mathematical space based on some measure.

Clustering can comprise grouping any number of samples in a dataset by some measure. In some embodiments, clustering can comprise K-means clustering. In some embodiments, clustering can comprise hierarchical clustering. In some embodiments, clustering can comprise using random forest models. In some embodiments, clustering can comprise boosted tree models. In some embodiments, clustering can comprise using support vector machines. In some embodiments, clustering can comprise calculating one or more N-1 dimensional surfaces in N-dimensional space that partitions a dataset into clusters. In some embodiments, clustering can comprise distribution-based clustering. In some embodiments, clustering can comprise fitting a plurality of prior distributions over the data distributed in N-dimensional space. In some embodiments, clustering can comprise using density-based clustering. In some embodiments, clustering can comprise using fuzzy clustering. In some embodiments, clustering can comprise computing probability values of a data point belonging to a cluster. In some embodiments, clustering can comprise using constraints. In some embodiments, clustering can comprise using supervised learning. In some embodiments, clustering can comprise using unsupervised learning.

In some embodiments, clustering can comprise grouping samples based on similarity. In some embodiments, clustering can comprise grouping samples based on quantitative similarity. In some embodiments, clustering can comprise grouping samples based on one or more features of each sample. In some embodiments, clustering can comprise grouping samples based on one or more labels of each sample. In some embodiments, clustering can comprise grouping samples based on Euclidean coordinates. In some embodiments, clustering can comprise grouping samples based the features of the nodes and edges of each sample.

In some embodiments, different clusters may be completely separate, such that different cluster share no elements (e.g., two clusters are mutually exclusive). In some embodiments, different clusters may share one or more elements, and at the same time not share one or more elements (e.g., two clusters may partially overlap). In some embodiments, one cluster may be enclosed by another cluster, such that all elements in one cluster are included in another cluster.

In some embodiments, comparing can comprise comparing between a first group and different second group. In some embodiments, a first or a second group can each independently be a cluster. In some embodiments, a first or a second group can each independently be a group of clusters. In some embodiments, comparing can comprise comparing between one cluster with a group of clusters. In some embodiments, comparing can comprise comparing between a first group of clusters with second group of clusters different than the first group. In some embodiments, one group can be one sample. In some embodiments, one group can be a group of samples. In some embodiments, comparing can comprise comparing between one sample versus a group of samples. In some embodiments, comparing can comprise comparing between a group of samples versus a group of samples.

Varied Machine Learning Techniques

In some cases, machine learning (ML) may generally involve identifying and recognizing patterns in existing data in order to facilitate making predictions for subsequent data. ML may include a ML model (which may include, for example, a ML algorithm). Machine learning, whether analytical or statistical in nature, may provide deductive or abductive inference based on real or simulated data. The ML model may be a trained model. ML techniques may comprise one or more supervised, semi-supervised, self-supervised, or unsupervised ML techniques. For example, an ML model may be a trained model that is trained through supervised learning (e.g., various parameters are determined as weights or scaling factors). ML may comprise one or more of regression analysis, regularization, classification, dimensionality reduction, ensemble learning, meta learning, association rule learning, cluster analysis, anomaly detection, deep learning, or ultra-deep learning. ML may comprise, but is not limited to: k-means, k-means clustering, k-nearest neighbors, learning vector quantization, linear regression, non-linear regression, least squares regression, partial least squares regression, logistic regression, stepwise regression, multivariate adaptive regression splines, ridge regression, principal component regression, least absolute shrinkage and selection operation (LASSO), least angle regression, canonical correlation analysis, factor analysis, independent component analysis, linear discriminant analysis, multidimensional scaling, non-negative matrix factorization, principal components analysis, principal coordinates analysis, projection pursuit, Sammon mapping, t-distributed stochastic neighbor embedding, AdaBoosting, boosting, gradient boosting, bootstrap aggregation, ensemble averaging, decision trees, conditional decision trees, boosted decision trees, gradient boosted decision trees, random forests, stacked generalization, Bayesian networks, Bayesian belief networks, naive Bayes, Gaussian naive Bayes, multinomial naive Bayes, hidden Markov models, hierarchical hidden Markov models, support vector machines, encoders, decoders, auto-encoders, stacked auto-encoders, perceptrons, multi-layer perceptrons, artificial neural networks, feedforward neural networks, convolutional neural networks, recurrent neural networks, long short-term memory, deep belief networks, deep Boltzmann machines, deep convolutional neural networks, deep recurrent neural networks, or generative adversarial networks.

Training the ML model may include, in some cases, selecting one or more untrained data models to train using a training data set. The selected untrained data models may include any type of untrained ML models for supervised, semi-supervised, self-supervised, or unsupervised machine learning. The selected untrained data models be specified based upon input (e.g., user input) specifying relevant parameters to use as predicted variables or other variables to use as potential explanatory variables. For example, the selected untrained data models may be specified to generate an output (e.g., a prediction) based upon the input. Conditions for training the ML model from the selected untrained data models may likewise be selected, such as limits on the ML model complexity or limits on the ML model refinement past a certain point. The ML model may be trained (e.g., via a computer system such as a server) using the training data set. In some cases, a first subset of the training data set may be selected to train the ML model. The selected untrained data models may then be trained on the first subset of training data set using appropriate ML techniques, based upon the type of ML model selected and any conditions specified for training the ML model. In some cases, due to the processing power requirements of training the ML model, the selected untrained data models may be trained using additional computing resources (e.g., cloud computing resources). Such training may continue, in some cases, until at least one aspect of the ML model is validated and meets selection criteria to be used as a predictive model.

In some cases, one or more aspects of the ML model may be validated using a second subset of the training data set (e.g., distinct from the first subset of the training data set) to determine accuracy and robustness of the ML model. Such validation may include applying the ML model to the second subset of the training data set to make predictions derived from the second subset of the training data. The ML model may then be evaluated to determine whether performance is sufficient based upon the derived predictions. The sufficiency criteria applied to the ML model may vary depending upon the size of the training data set available for training, the performance of previous iterations of trained models, or user-specified performance requirements. If the ML model does not achieve sufficient performance, additional training may be performed. Additional training may include refinement of the ML model or retraining on a different first subset of the training dataset, after which the new ML model may again be validated and assessed. When the ML model has achieved sufficient performance, in some cases, the ML may be stored for present or future use. The ML model may be stored as sets of parameter values or weights for analysis of further input (e.g., further relevant parameters to use as further predicted variables, further explanatory variables, further user interaction data, etc.), which may also include analysis logic or indications of model validity in some instances. In some cases, a plurality of ML models may be stored for generating predictions under different sets of input data conditions. In some embodiments, the ML model may be stored in a database (e.g., associated with a server).

Neural Network Architecture

In some embodiments, systems and methods of the present disclosure may comprise or comprise using a neural network. The neural network may comprise various architectures, loss functions, optimization algorithms, assumptions, and various other neural network design choices. In some embodiments, the neural network comprises an encoder. In some embodiments, the neural network comprises a decoder. In some embodiments, the neural network comprises a bottleneck architecture comprising the encoder and the decoder. In some embodiments, the bottleneck architecture comprises a U-net. In some embodiments, the bottleneck architecture comprises an autoencoder.

In some embodiments, the neural network comprises a language model. In some embodiments, the language model is a long-short-term-memory model (LSTM). In some embodiments, the language model is a convolutional neural network. In some embodiments, the language model is an autoregressive model. As used herein, a language model may refer to any neural network or algorithm configured to output a semantically correct and interpretable representation of a chemical, material, or both.

In some embodiments, the neural network comprises a convolutional layer. In some embodiments, the neural network comprises a densely-connected layer. In some embodiments, the neural network comprises a skip connection. In some embodiments, the neural network may comprise graph convolutional layers. In some embodiments, the neural network may comprise message passing layers. In some embodiments, the neural network may comprise attention layers. In some embodiments, the neural network may comprise recurrent layers. In some embodiments, the neural network may comprise a gated recurrent unit. In some embodiments, the neural network may comprise reversible layers. In some embodiments, the neural network may comprise a neural network with a bottleneck layer. In some embodiments, the neural network may comprise residual blocks. In some embodiments, the neural network may comprise one or more dropout layers. In some embodiments, the neural network may comprise one or more batch normalization layers. In some embodiments, the neural network may comprise one or more pooling layers. In some embodiments, the neural network may comprise one or more upsampling layers. In some embodiments, the neural network may comprise one or more max-pooling layers. Various types of layers may be used a neural network without departing from the inventive concepts disclosed herein.

In some embodiments, the neural network comprises a graph model. In some embodiments, a graph, graph model, and graphical model can refer to a method that models data in a graphical representation comprising nodes and edges. In some embodiments, the data may be stored in a various and alternative forms such as linked lists, dictionaries, spreadsheets, arrays, in permanent storage, in transient storage, and so on, and is not limited to specific embodiments disclosed herein.

In some embodiments, the neural network may comprise an autoencoder. In some embodiments, the neural network may comprise a variational autoencoder. In some embodiments, the neural network may comprise a generative adversarial network. In some embodiments, the neural network may comprise a flow model. In some embodiments, the neural network may comprise an autoregressive model.

The neural network may comprise various activation functions. In some embodiments, an activation function may be a non-linearity. In some embodiments, the neural network may comprise one or more activation function. In some embodiments, the neural network may comprise a ReLU, softmax, tanh, sigmoid, softplus, softsign, selu, elu, exponential, LeakyReLU, or any combination thereof. Various activation functions may be used with a neural network, without departing from the inventive concepts disclosed herein.

In some embodiments, the neural network may comprise a regression loss function. In some embodiments, the neural network may comprise a logistic loss function. In some embodiments, the neural network may comprise a variational loss. In some embodiments, the neural network may comprise a prior. In some embodiments, the neural network may comprise a Gaussian prior. In some embodiments, the neural network may comprise a non-Gaussian prior. In some embodiments, the neural network may comprise an adversarial loss. In some embodiments, the neural network may comprise a reconstruction loss. In some embodiments, the neural network may be trained with the Adam optimizer. In some embodiments, the neural network may be trained with the stochastic gradient descent optimizer. In some embodiments, the neural network hyperparameters are optimized with Gaussian Processes. In some embodiments, the neural network may be trained with train/validation/test data splits. In some embodiments, the neural network may be trained with k-fold data splits, with any positive integer for k. A neural network may be trained with various loss functions whose derivatives may be computed to update one or more parameters of the neural network. A neural network may be trained with hyperparameter searching algorithms.

Training

In some aspects, the present disclosure describes a method of machine learning an engineered chemical space.

In some embodiments, the method may comprise providing a neural network. In some embodiments, the neural network may comprise an input layer configured to receive at least a target descriptor. In some embodiments, the neural network may comprise a latent layer configured to output at least a latent descriptor, wherein the latent layer is connected to the input layer. In some embodiments, the neural network may comprise an output layer configured to output at least a target-ligand interaction descriptor, wherein the output layer is connected to the latent layer. In some embodiments, the neural network may comprise a second output layer configured to output at least a ligand descriptor, wherein the second output layer is connected to the latent layer. In some embodiments, the neural network further comprises a plurality of hidden layers connecting at least two of: the input layer, the latent layer, and first output layer, and the second output layer. In some embodiments, the neural network may comprise at least one parameter. In some embodiments, a layer in the neural network may comprise at least one parameter.

In some embodiments, the method may comprise providing training data. In some embodiments, the training data may comprise a plurality of target descriptors. In some embodiments, the training data may comprise a plurality of target-ligand interaction descriptors. In some embodiments, the training data may comprise a plurality of ligand latent descriptors. In some embodiments, the training data may comprise a plurality of ligand descriptors. In some embodiments, the plurality of target descriptors of the training data comprises features that describe at least one of: hydrophobicity, aromaticity, hydrogen bond accepting, hydrogen bond donating, positive ionizability, negative ionizability, metallicity, pocket occupancy, hydrogen bond interaction ability, hydrophobic interaction ability, pi-pi interaction ability, and halogen interaction ability. In some embodiments, the plurality of target-ligand interaction descriptors in the training data comprises ligand occupancy of a given target. In some embodiments, the plurality of ligand latent descriptors in the training data comprises SMILES of a given ligand.

In some embodiments, the method may comprise training the neural network. In some embodiments, the training the neural network may comprise inputting at least the plurality of target descriptors at the input layer of the neural network. In some embodiments, the training the neural network may comprise outputting a plurality of output latent descriptors at the latent layer and a plurality of output target-ligand interaction descriptors at the output layer. In some embodiments, the training the neural network may comprise optimizing a plurality of loss functions based at least in part on the plurality of output latent descriptors and the plurality of output target-ligand interaction descriptors. In some embodiments, the training the neural network may comprise updating the at least one parameter of the neural network. In some embodiments, the training of the neural network may comprise guiding the neural network to learn the engineered chemical space comprising a unified embedding for at least the plurality of target descriptors and the plurality of ligand latent descriptors.

In some embodiments, the engineered chemical space is at least partially organized based on spatial information of the plurality of target descriptors and/or chemical structure information from the plurality of ligand latent descriptors. In some embodiments, in the engineered chemical space, a given target latent descriptor of a given target has a similarity with a given ligand latent descriptor of a given ligand when the given ligand targets the given target, and has a dissimilarity when the given ligand does not target the given target. In some embodiments, the given target latent descriptor is not identical to the given ligand latent descriptor. In some embodiments, the similarity or the dissimilarity is measurable using a similarity function.

In some embodiments, the plurality of loss functions comprises a contrastive loss function computed between a plurality of pairs formed between a plurality of target latent descriptors output by the latent layer and the plurality ligand latent descriptors. In some embodiments, at least a portion of the plurality of pairs may be formed between one target latent descriptor and numerous ligand latent descriptor. In some embodiments, at least a portion of the plurality of pairs may be formed between one ligand latent descriptor and numerous target latent descriptors. In some embodiments, the plurality of pairs may be formed randomly or following a predetermined pattern or protocol (e.g., within batches of training data). In some embodiments, a pair may be formed between a ligand latent descriptor and a target latent descriptor that is expected to be similar. In some embodiments, a pair may be formed between a ligand latent descriptor and a target latent descriptor that is expected to be different.

In some embodiments, at least a portion of the neural network is trained at least in part by using a learning method that embeds two or more source of information into a unified embedding space. In some embodiments, the learning method is contrastive learning. In some embodiments, the contrastive learning is based at least in part on optimizing a loss function computed between pairs of target latent descriptors and ligand latent descriptors in a training data. In some embodiments, the loss function comprises a contrastive loss function.

In some embodiments, the contrastive loss comprises at least:

$$L(p,f) = [a - \text{sim}(p,f) + \text{sim}(p,f')]_+ + [a - \text{sim}(p,f) + \text{sim}(p',f)]_+$$

wherein $L(p,f)$ denotes the contrastive loss, a is a margin parameter, p is a first target descriptor in a training data, f is a first ligand descriptor in the training data, p' is a second target descriptor in the training data that is least similar to the first ligand descriptor, f' is a second ligand descriptor in the training data that is least similar to the first target descriptor, sim is a similarity function computed between its parentheticals, and $[x]_+ = \max(x,0)$.

In some embodiments, the training the neural network comprises optimizing a loss function comprising a reconstruction loss function computed between the plurality of target-ligand interaction descriptors of the training data and a plurality of reconstructed target-ligand interaction descriptors output by the first output layer.

In some embodiments, at least a portion of the neural network is trained at least in part on a learning method that parameterizes the portion of the neural network to output a ligand-target interaction descriptor. In some embodiments, the learning method comprises optimizing a reconstruction loss function based at least in part on ligand occupancy.

In some embodiments, the reconstruction loss comprises at least:

$$L(X_o, Y_o) = \|X_o - Y_o\|_2^2$$

wherein $L(X_o, Y_o)$ denotes the reconstruction loss, wherein $X_o$ is a ligand occupancy descriptor in the training data, and wherein $Y_o$ is a reconstruction of the ligand occupancy descriptor by at least a portion the neural network.

In some embodiments, the reconstruction loss may be calculated between data that describes an interaction between a target and a ligand. In some embodiments, the interaction may comprise covalent bonding interactions, hydrogen bonding interactions, electrostatic interactions, or ionic interactions. In some embodiments, the interaction may comprise a chemical reaction. In some embodiments, the interaction may comprise conformational change induced by the ligand on the target. In some embodiments, the interaction may comprise reversible binding. In some embodiments, the interaction may comprise irreversible binding.

In some embodiments, the training the neural network comprises outputting a plurality of output ligand descriptors, and optimizing a loss function comprising a reconstruction loss function computed between the plurality of target-ligand descriptors of the training data and a plurality of output target-ligand interaction descriptors output by the second output layer.

In some embodiments, at least a portion of the neural network is trained at least in part on a learning method that parameterizes the portion of the neural network to output molecular identifiers. In some embodiments, the learning method is optimizing a reconstruction loss. In some embodiments, the reconstruction loss is a probabilistic loss. In some embodiments, the reconstruction loss comprises at least:

$$L(X_f, Y_f) = -\Sigma_i^n Y_{f,i} \cdot \log(X_{f,i})$$

wherein $L(X_f, Y_f)$ denotes the reconstruction loss, wherein $-\Sigma_i^n$ denotes a negative summation over each element i of in a total of n elements in the operands, wherein $X_{f,i}$ is a ligand identifier element in the training data, and wherein $Y_{f,i}$ is a ligand identifier element that is reconstructed by at least a portion the neural network.

Various other forms of loss functions may be used. For example, In some embodiments, the loss functions may be formulated to optimize a regression loss, an evidence-based lower bound, a maximum likelihood, Kullback-Leibler divergence, applied with various distribution functions such as Gaussians, non-Gaussian, mixtures of Gaussians, mixtures of logistic functions, and so on.

In some aspects, the present disclosure describes a computer-implemented method, implementing a method of training a neural network on a computer.

In some aspects, the present disclosure describes a computer program product comprising a computer-readable medium having computer-executable code encoded therein, the computer-executable code adapted to be executed to implement a method of training a neural network.

In some aspects, the present disclosure describes a non-transitory computer-readable storage media encoded with a computer program including instructions executable by one or more processors to train a neural network.

In some aspects, the present disclosure describes a computer-implemented system comprising: a digital processing device comprising: at least one processor, an operating system configured to perform executable instructions, a memory, and a computer program including instructions executable by the digital processing device to train a neural network.

Latent Descriptor Generation

In some embodiments, a latent descriptor may be generated using a target descriptor encoder.

In some embodiments, the target descriptor encoder may be a portion of a neural network. In some embodiments, the target descriptor encoder receives a target descriptor and transforms the target descriptor to a latent descriptor.

In some embodiments, a latent descriptor may be generated using a ligand identifier encoder. In some embodiments, the ligand identifier encoder may perform fingerprinting based at least in part on a given ligand descriptor. In some embodiments, the fingerprinting may generate a Morgan fingerprint, a Tanimoto fingerprint, or any other fingerprint. In some embodiments, the ligand identifier encoder may be a portion of a neural network. In some embodiments, the ligand identifier encoder may transform a given ligand descriptor into a latent descriptor.

The latent descriptor may be embedded on various supports. A support may comprise any sufficient number of dimensions. The sufficient number dimensions may vary based at least in part on the complexity of the dataset, size of the dataset, type of embedding used, and other factors. A support may comprise various geometries. In some embodiments, a support may comprise a dimension that extends from negative infinity to positive infinity. In some embodiments, a support may comprise a dimension is periodic, for example, from zero to two pi radians. The latent descriptor may be embedded in the engineering chemical space to comprise various manifold shapes.

Ligand Descriptor Generation

In some embodiments, the generating the ligand descriptor is performed using a neural network. In some embodiments, the generating the ligand descriptor is performed using a language model. In some embodiments, the generating the ligand descriptor is performed stochastically. In some embodiments, the generating the ligand descriptor is performed with sampling noise. In some embodiments, the generating the ligand descriptor is performed by receiving a latent descriptor and transforming the latent descriptor into a ligand descriptor.

In some embodiments, the ligand descriptor comprises a ligand identifier. In some embodiments, the ligand identifier comprises a textual identifier. In some embodiments, the textual identifier comprises SMILES, InChI (and its various subtypes), or SELFIES. In some embodiments, the ligand identifier comprises a molecular adjacency matrix or a molecular graph. In some embodiments, the ligand identifier can be any descriptor that unambiguously describes a ligand.

In some embodiments, the ligand descriptor may comprise a molecular fingerprint. Various molecular fingerprinting methods may be used to create a molecular fingerprint. In some embodiments, the molecular fingerprint may be a Morgan fingerprint, a Tanimoto fingerprint, multilevel neighborhoods of atoms, spectrophores, or any combination thereof. In some embodiments, the molecular fingerprint may be generated using radial basis functions, graph convolutions, latent space engineering using a neural network, or any combination thereof.

In some embodiments, the language model comprises a neural network. In some embodiments, the language model comprises a long-short-term-memory model (LSTM). In some embodiments, hidden units of the LSTM are initialized with the ligand descriptor. In some embodiments, the language model comprises a gated recurrent unit (GRU). In some embodiments, hidden units of the GRU are initialized with the ligand descriptor. In some embodiments, the language model comprises one or more dense layers.

Interaction Descriptor Generation

In some embodiments, the generating the target-ligand interaction descriptor is performed using a neural network. In some embodiments, the generating the target-ligand interaction descriptor is performed deterministically. In some embodiments, the generating the target-ligand interaction descriptor is performed stochastically. In some embodiments, the generating the target-ligand interaction descriptor is performed with sampling noise. In some embodiments, the generating the target-ligand interaction descriptor is performed by receiving a latent descriptor and transforming the latent descriptor into a target-ligand interaction descriptor.

In some embodiments, a target-ligand interaction descriptor may comprise information that describes an interaction between a given ligand and a given target. In some embodiments, the information may comprise ligand occupancy of the target. In some embodiments, the information may comprise a change in a chemical structure of a ligand, a target, or both. In some embodiments, the information may comprise a change in a conformation of a ligand, a target, or both. In some embodiments, the information may comprise bonds formed between a ligand and a target.

Training Data

Various target descriptors may be used. In some embodiments, the target descriptor comprises a protein target descriptor. In some embodiments, the target descriptor comprises a protein pocket descriptor. In some embodiments, the target descriptor comprises features that describe at least one of: hydrophobicity, aromaticity, hydrogen bond accepting property, hydrogen bond donating property, positive ionizability, negative ionizability, metallicity, pocket occupancy, hydrogen bond interaction ability, hydrophobic interaction ability, pi-pi interaction ability, halogen interaction ability, and ligand occupancy. In some embodiments, the target descriptor comprises a spatial map of one or more protein targets. In some embodiments, the spatial map is a grid. In some embodiments, the spatial map is a rectangular grid. In some embodiments, the spatial map comprises at least 3 dimensions. In some embodiments, the spatial map comprises at least 4 dimensions. In some embodiments, the spatial map comprises a resolution less than about 3.5 Angstroms. In some embodiments, the spatial map comprises a resolution less than about 0.1, 0.2, 0.3, 0.4, 0.5, 0.6, 0.7, 0.8, 0.9, 1, 2, 3, 4, 5, 6, 7, 8, 9, or 10 Angstroms, including increments therein. In some embodiments, the spatial map comprises a resolution more than about 0.1, 0.2, 0.3, 0.4, 0.5, 0.6, 0.7, 0.8, 0.9, 1, 2, 3, 4, 5, 6, 7, 8, 9, or 10 Angstroms, including increments therein.

Various ligand descriptors may be used. In some embodiments, the ligand descriptor comprises a small molecule identifier. In some embodiments, the ligand descriptor comprises large molecule identifier. In some embodiments, the ligand descriptor comprises a chemical structure identifier. In some embodiments, the ligand descriptor comprises SMILES. In some embodiments, the ligand descriptor comprises SELFIES, InChi, an adjacency matrix, a graph, molecular coordinates, vibrational spectra, molecular fingerprints, or any combination thereof. In some embodiments, the ligand descriptor comprises a latent descriptor of a ligand descriptor, for example, a latent descriptor of SMILES, SELFIES, InChi, a graph, molecular fingerprints, or any combination thereof.

In some embodiments, the target descriptor may be normalized. In some embodiments, the ligand descriptor may be normalized. In some embodiments, the term normalizing can refer to a collection of methods for adjusting a dataset to align the dataset to a common scale. In some embodiments, a normalizing method can comprise multiplying a portion or the entirety of a dataset by a factor. In some embodiments, a normalizing method can comprise adding or subtracting a constant from a portion or the entirety of a dataset. In some embodiments, a normalizing method can comprise adjusting a portion or the entirety of a dataset to a known statistical distribution. In some embodiments, a normalizing method can comprise adjusting a portion or the entirety of a dataset to a normal distribution. In some embodiments, a normalizing method can comprise adjusting the dataset so that the signal strength of a portion or the entirety of a dataset is about the same.

Inference

In some aspects, the present disclosure describes systems and methods for generating a ligand identifier.

In some embodiments, a ligand identifier may be generated based at least in part on a latent descriptor. In some embodiments, a ligand identifier may be generated deterministically. In some embodiments, a ligand identifier may be generated stochastically. In some embodiments, a ligand identifier may be generated with added noise. In some embodiments, a ligand identifier may be generated based at least on human input. In some embodiments, the human input may comprise navigation of the engineered chemical space.

Figure 4:
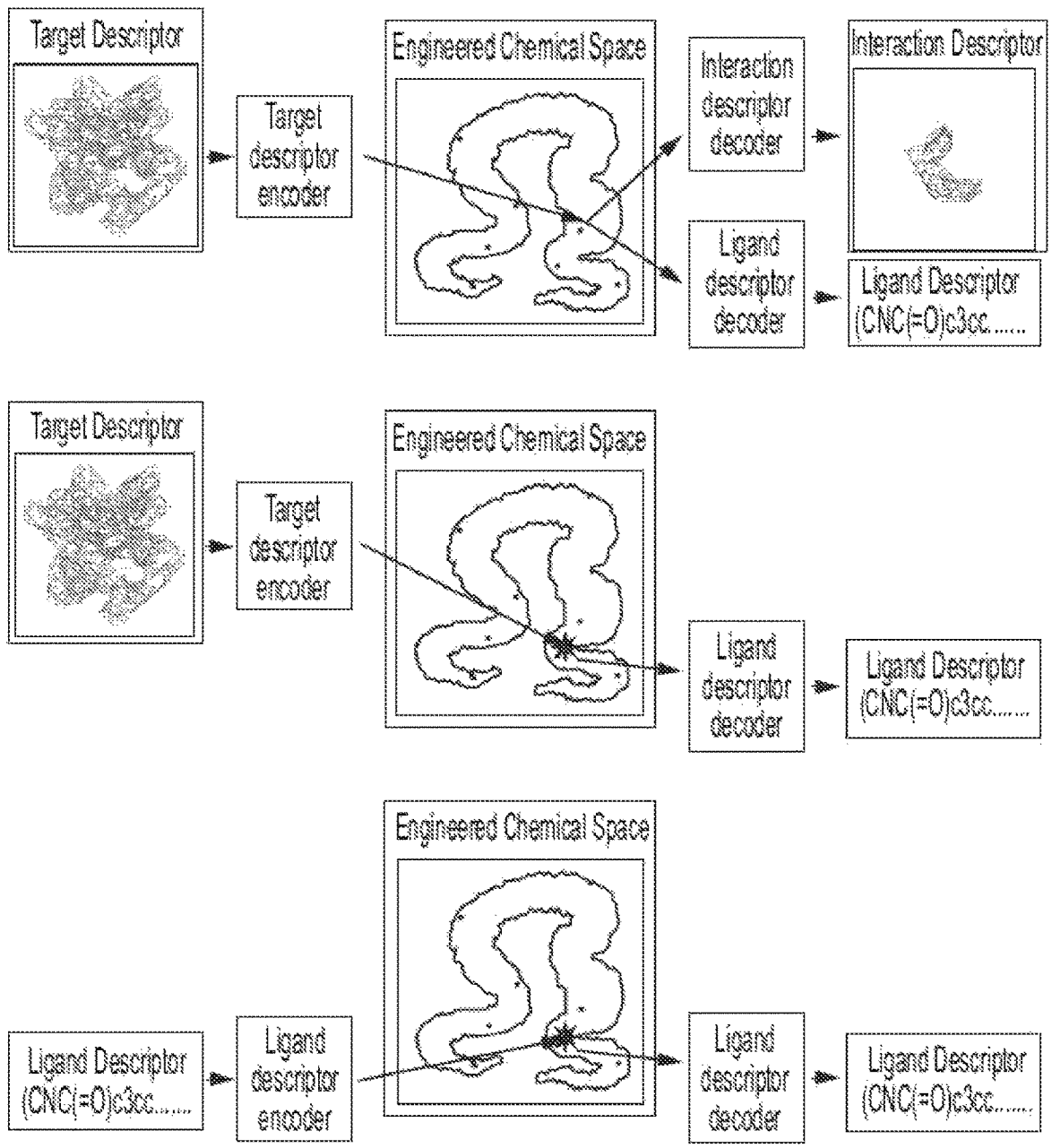
FIG. 4 illustrates inference methods, in accordance with some embodiments. The top panel shows an inference method that receives a target descriptor of a target as input, and outputs ligand occupancy of the target and/or a ligand identifier for a candidate ligand that is predicted to bind with the target. The middle panel shows an inference method that receives a target descriptor of a target as input to output a latent descriptor in the engineered chemical space, which may be navigated (e.g., by adding noise) to select a different latent descriptor, and where the latent descript is used to output a candidate ligand that is predicted to bind with the target. The bottom panel shows an inference method that receives a ligand identifier as input to output a latent descriptor in the engineered chemical space, which may be navigated to select a different latent descriptor, and where the latent descriptor is used to output a new candidate ligand that may target similar targets as the ligand of the input ligand descriptor.

FIG. 4, top panel shows an inference method that receives a target descriptor of a target as input, and outputs ligand occupancy of the target and/or a ligand identifier for a candidate ligand that is predicted to bind with the target. In some embodiments, a latent descriptor may be generated based at least in part on a target descriptor. In some embodiments, a ligand descriptor may be generated based at least in part on a latent descriptor. In some embodiments, a target-ligand interaction descriptor may be generated based at least in part on a latent descriptor.

In some embodiments, a target descriptor may be a spatial map of a protein pocket. In some embodiments, a target descriptor encoder may transform a target descriptor into a latent descriptor in the engineered chemical space. In some embodiments, a latent descriptor decoder may transform a latent descriptor into a ligand descriptor. In some embodiments, a target descriptor decoder transforms a latent descriptor into a target-ligand interaction descriptor.

FIG. 4, middle panel shows an inference method that receives a target descriptor of a target as input to output a latent descriptor in the engineered chemical space, which may be navigated (e.g., by adding noise) to select a different latent descriptor, and outputs a candidate ligand that is predicted to bind with the target. FIG. 4, bottom panel shows an inference method that receives a ligand identifier as input to output a latent descriptor in the engineered chemical space, which may be navigated to select a different latent descriptor, and outputs a new candidate ligand that may target similar targets as the ligand of the input ligand descriptor. In some embodiments, the engineered chemical space may have organized latent descriptors such that the proximal latent descriptors map to ligands that target similar targets.

In some embodiments, a second latent descriptor may be generated based at least in part on a first latent descriptor. In some embodiments, the second latent descriptor may be generated automatically or by incorporating input from a human being. In some embodiments, the second descriptor may be generated by adding white or structured noise to the first latent descriptor. In some embodiments, the second descriptor may be generated based on human input to navigate an engineered chemical space.

In some aspects, the present disclosure describes a computer-implemented method, implementing a method of sampling a ligand descriptor or a target-ligand interaction descriptor on a computer.

In some aspects, the present disclosure describes a computer program product comprising a computer-readable medium having computer-executable code encoded therein, the computer-executable code adapted to be executed to implement a method of sampling a ligand descriptor or a target-ligand interaction descriptor.

In some aspects, the present disclosure describes a non-transitory computer-readable storage media encoded with a computer program including instructions executable by one or more processors to sample a ligand descriptor or a target-ligand interaction descriptor.

In some aspects, the present disclosure describes a computer-implemented system comprising: a digital processing device comprising: at least one processor, an operating system configured to perform executable instructions, a memory, and a computer program including instructions executable by the digital processing device to sample a ligand descriptor or a target-ligand interaction descriptor.

Computing System

Figure 5:
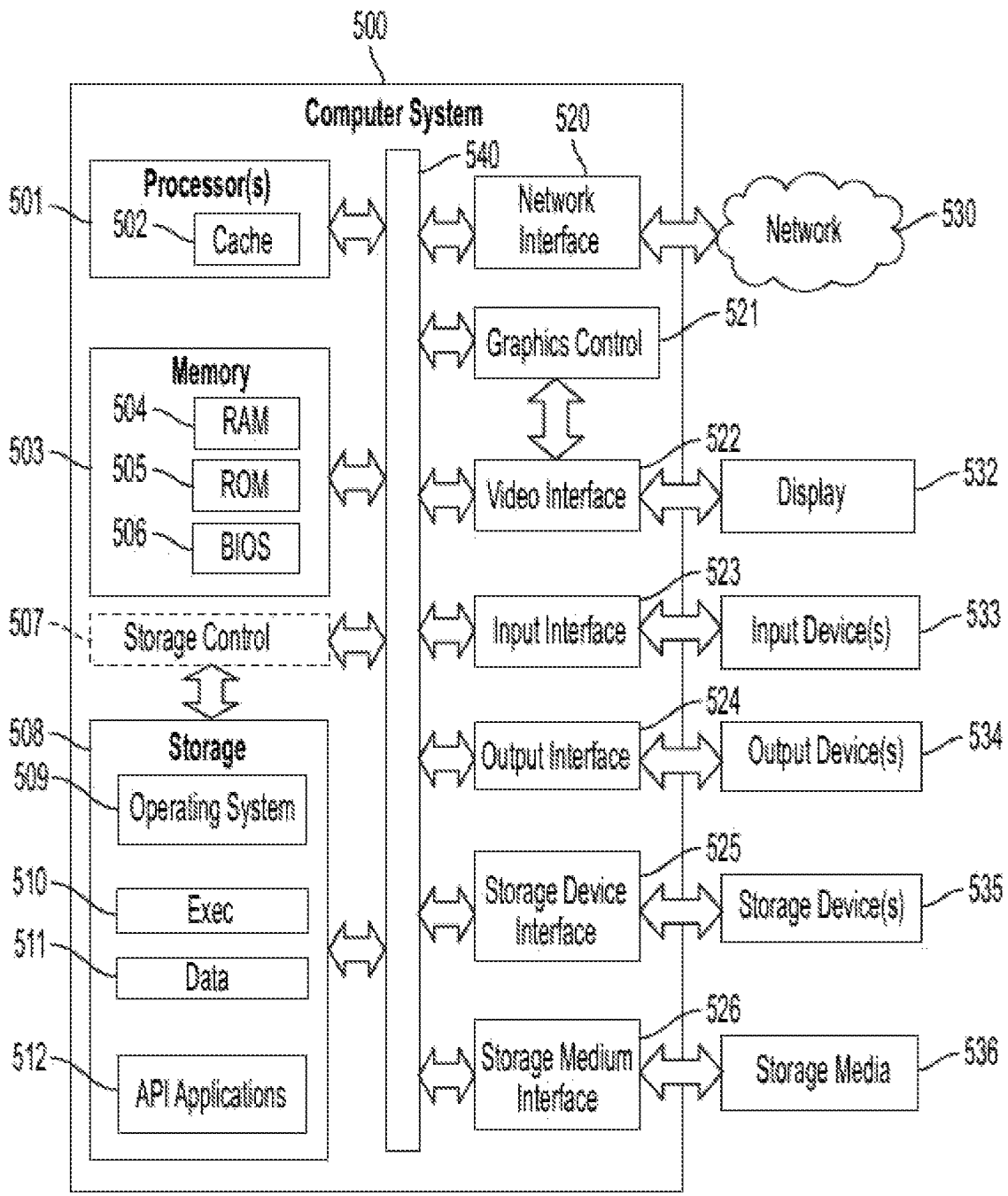
FIG. 5 shows a non-limiting example of a computing device; in this case, a device with one or more processors, memory, storage, and a network interface.

In some aspects, the present disclosure describes a computer-implemented system comprising: a digital processing device comprising: at least one processor, an operating system configured to perform executable instructions, a memory, and a computer program including instructions executable by the digital processing device to sample a ligand using any one of the methods disclosed herein. In some aspects, the present disclosure describes a computer-implemented method, implementing any one of the methods disclosed herein in a computer system. Referring to FIG. 5, a block diagram is shown depicting an exemplary machine that includes a computer system 500 (e.g., a processing or computing system) within which a set of instructions can execute for causing a device to perform or execute any one or more of the aspects and/or methodologies for sampling a ligand or training a neural network to learn an engineered chemical space of the present disclosure. The components in FIG. 5 are examples only and do not limit the scope of use or functionality of any hardware, software, embedded logic component, or a combination of two or more such components implementing particular embodiments.

Computer system 500 may include one or more processors 501, a memory 503, and a storage 508 that communicate with each other, and with other components, via a bus 540. The bus 540 may also link a display 532, one or more input devices 533 (which may, for example, include a keypad, a keyboard, a mouse, a stylus, etc.), one or more output devices 534, one or more storage devices 535, and various tangible storage media 536. All of these elements may interface directly or via one or more interfaces or adaptors to the bus 540. For instance, the various tangible storage media 536 can interface with the bus 540 via storage medium interface 526. Computer system 500 may have any suitable physical form, including but not limited to one or more integrated circuits (ICs), printed circuit boards (PCBs), mobile handheld devices (such as mobile telephones or PDAs), laptop or notebook computers, distributed computer systems, computing grids, or servers.

Computer system 500 includes one or more processor(s) 501 (e.g., central processing units (CPUs), general purpose graphics processing units (GPGPUs), or quantum processing units (QPUs)) that carry out functions. Computer system 500 may be one of various high performance computing platforms. For instance, the one or more processor(s) 501 may form a high performance computing cluster. In some embodiments, the one or more processors 501 may form a distributed computing system connected by wired and/or wireless networks. In some embodiments, arrays of CPUs, GPUs, QPUs, or any combination thereof may be operably linked to implement any one of the methods disclosed herein. Processor(s) 501 optionally contains a cache memory unit 502 for temporary local storage of instructions, data, or computer addresses. Processor(s) 501 are configured to assist in execution of computer readable instructions. Computer system 500 may provide functionality for the components depicted in FIG. 5 as a result of the processor(s) 501 executing non-transitory, processor-executable instructions embodied in one or more tangible computer-readable storage media, such as memory 503, storage 508, storage devices 535, and/or storage medium 536. The computer-readable media may store software that implements particular embodiments, and processor(s) 501 may execute the software. Memory 503 may read the software from one or more other computer-readable media (such as mass storage device(s) 535, 536) or from one or more other sources through a suitable interface, such as network interface 520. The software may cause processor(s) 501 to carry out one or more processes or one or more steps of one or more processes described or illustrated herein. Carrying out such processes or steps may include defining data structures stored in memory 503 and modifying the data structures as directed by the software.

The memory 503 may include various components (e.g., machine readable media) including, but not limited to, a random access memory component (e.g., RAM 504) (e.g., static RAM (SRAM), dynamic RAM (DRAM), ferroelectric random access memory (FRAM), phase-change random access memory (PRAM), etc.), a read-only memory component (e.g., ROM 505), and any combinations thereof. ROM 505 may act to communicate data and instructions unidirectionally to processor(s) 501, and RAM 504 may act to communicate data and instructions bidirectionally with processor(s) 501. ROM 505 and RAM 504 may include any suitable tangible computer-readable media described below. In one example, a basic input/output system 506 (BIOS), including basic routines that help to transfer information between elements within computer system 500, such as during start-up, may be stored in the memory 503.

Fixed storage 508 is connected bidirectionally to processor(s) 501, optionally through storage control unit 507. Fixed storage 508 provides additional data storage capacity and may also include any suitable tangible computer-readable media described herein. Storage 508 may be used to store operating system 509, executable(s) 510, data 511, applications 512 (application programs), and the like. Storage 508 can also include an optical disk drive, a solid-state memory device (e.g., flash-based systems), or a combination of any of the above. Information in storage 508 may, in appropriate cases, be incorporated as virtual memory in memory 503.

In one example, storage device(s) 535 may be removably interfaced with computer system 500 (e.g., via an external port connector (not shown)) via a storage device interface 525. Particularly, storage device(s) 535 and an associated machine-readable medium may provide non-volatile and/or volatile storage of machine-readable instructions, data structures, program modules, and/or other data for the computer system 500. In one example, software may reside, completely or partially, within a machine-readable medium on storage device(s) 535. In another example, software may reside, completely or partially, within processor(s) 501.

Bus 540 connects a wide variety of subsystems. Herein, reference to a bus may encompass one or more digital signal lines serving a common function, where appropriate. Bus 540 may be any of several types of bus structures including, but not limited to, a memory bus, a memory controller, a peripheral bus, a local bus, and any combinations thereof, using any of a variety of bus architectures. As an example, and not by way of limitation, such architectures include an Industry Standard Architecture (ISA) bus, an Enhanced ISA (EISA) bus, a Micro Channel Architecture (MCA) bus, a Video Electronics Standards Association local bus (VLB), a Peripheral Component Interconnect (PCI) bus, a PCI-Express (PCI-X) bus, an Accelerated Graphics Port (AGP) bus, HyperTransport (HTX) bus, serial advanced technology attachment (SATA) bus, and any combinations thereof.

Computer system 500 may also include an input device 533. In one example, a user of computer system 500 may enter commands and/or other information into computer system 500 via input device(s) 533. Examples of an input device(s) 533 include, but are not limited to, an alpha-numeric input device (e.g., a keyboard), a pointing device (e.g., a mouse or touchpad), a touchpad, a touch screen, a multi-touch screen, a joystick, a stylus, a gamepad, an audio input device (e.g., a microphone, a voice response system, etc.), an optical scanner, a video or still image capture device (e.g., a camera), and any combinations thereof. In some embodiments, the input device is a Kinect, Leap Motion, or the like. Input device(s) 533 may be interfaced to bus 540 via any of a variety of input interfaces 523 (e.g., input interface 523) including, but not limited to, serial, parallel, game port, USB, FIREWIRE, THUNDERBOLT, or any combination of the above. In some embodiments, an input device 533 may be used to navigate the engineered chemical space and/or manipulate a visualization thereof. In some embodiments, a visual representation of an engineered chemical space may be enlarged, shrunk, rotated, reflected along an axis or plane, etc. using human inputs through an input device 533.

In particular embodiments, when computer system 500 is connected to network 530, computer system 500 may communicate with other devices, specifically mobile devices and enterprise systems, distributed computing systems, cloud storage systems, cloud computing systems, and the like, connected to network 530. Communications to and from computer system 500 may be sent through network interface

520. For example, network interface 520 may receive incoming communications (such as requests or responses from other devices) in the form of one or more packets (such as Internet Protocol (IP) packets) from network 530, and computer system 500 may store the incoming communications in memory 503 for processing. Computer system 500 may similarly store outgoing communications (such as requests or responses to other devices) in the form of one or more packets in memory 503 and communicated to network 530 from network interface 520. Processor(s) 501 may access these communication packets stored in memory 503 for processing.

Examples of the network interface 520 include, but are not limited to, a network interface card, a modem, and any combination thereof. Examples of a network 530 or network segment 530 include, but are not limited to, a distributed computing system, a cloud computing system, a wide area network (WAN) (e.g., the Internet, an enterprise network), a local area network (LAN) (e.g., a network associated with an office, a building, a campus or other relatively small geographic space), a telephone network, a direct connection between two computing devices, a peer-to-peer network, and any combinations thereof. A network, such as network 530, may employ a wired and/or a wireless mode of communication. In general, any network topology may be used.

Information and data can be displayed through a display 532. Examples of a display 532 include, but are not limited to, a cathode ray tube (CRT), a liquid crystal display (LCD), a thin film transistor liquid crystal display (TFT-LCD), an organic liquid crystal display (OLED) such as a passive-matrix OLED (PMOLED) or active-matrix OLED (AMOLED) display, a plasma display, and any combinations thereof. The display 532 can interface to the processor(s) 501, memory 503, and fixed storage 508, as well as other devices, such as input device(s) 533, via the bus 540. The display 532 is linked to the bus 540 via a video interface 522, and transport of data between the display 532 and the bus 540 can be controlled via the graphics control 521. In some embodiments, the display is a video projector. In some embodiments, the display is a head-mounted display (HMD) such as a VR headset. In further embodiments, suitable VR headsets include, by way of non-limiting examples, HTC Vive, Oculus Rift, Samsung Gear VR, Microsoft HoloLens, Razer OSVR, FOVE VR, Zeiss VR One, Avegant Glyph, Freefly VR headset, and the like. In still further embodiments, the display is a combination of devices such as those disclosed herein.

In addition to a display 532, computer system 500 may include one or more other peripheral output devices 534 including, but not limited to, an audio speaker, a printer, a storage device, and any combinations thereof. Such peripheral output devices may be connected to the bus 540 via an output interface 524. Examples of an output interface 524 include, but are not limited to, a serial port, a parallel connection, a USB port, a FIREWIRE port, a THUNDERBOLT port, and any combinations thereof.

In addition, or as an alternative, computer system 500 may provide functionality as a result of logic hardwired or otherwise embodied in a circuit, which may operate in place of or together with software to execute one or more processes or one or more steps of one or more processes described or illustrated herein. Reference to software in this disclosure may encompass logic, and reference to logic may encompass software. Moreover, reference to a computer-readable medium may encompass a circuit (such as an IC) storing software for execution, a circuit embodying logic for execution, or both, where appropriate. The present disclosure encompasses any suitable combination of hardware, software, or both.

Those of skill in the art will appreciate that the various illustrative logical blocks, modules, circuits, and algorithm steps described in connection with the embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality.

The various illustrative logical blocks, modules, and circuits described in connection with the embodiments disclosed herein may be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor may be a microprocessor, but in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration.

The steps of a method or algorithm described in connection with the embodiments disclosed herein may be embodied directly in hardware, in a software module executed by one or more processor(s), or in a combination of the two. A software module may reside in RAM memory, flash memory, ROM memory, EPROM memory, EEPROM memory, registers, hard disk, a removable disk, a CD-ROM, or any other form of storage medium known in the art. An exemplary storage medium is coupled to the processor such the processor can read information from, and write information to, the storage medium. In the alternative, the storage medium may be integral to the processor. The processor and the storage medium may reside in an ASIC. The ASIC may reside in a user terminal. In the alternative, the processor and the storage medium may reside as discrete components in a user terminal.

In accordance with the description herein, suitable computing devices include, by way of non-limiting examples, server computers, desktop computers, laptop computers, notebook computers, sub-notebook computers, netbook computers, netpad computers, set-top computers, media streaming devices, handheld computers, Internet appliances, mobile smartphones, and tablet computers.

In some embodiments, the computing device includes an operating system configured to perform executable instructions. The operating system is, for example, software, including programs and data, which manages the device's hardware and provides services for execution of applications. Those of skill in the art will recognize that suitable server operating systems include, by way of non-limiting examples, FreeBSD, OpenBSD, NetBSD®, Linux, Apple® Mac OS X Server®, Oracle® Solaris®, Windows Server®, and Novell® NetWare®. Those of skill in the art will recognize that suitable personal computer operating systems include, by way of non-limiting examples, Microsoft® Windows®, Apple® Mac OS X®, UNIX®, and UNIX-like operating systems such as GNU/Linux®. In some embodiments, the operating system is provided by cloud computing. Those of skill in the art will also recognize that suitable mobile smartphone operating systems include, by way of non-limiting examples, Nokia® Symbian® OS, Apple® Ios®, Research In Motion® BlackBerry OS®, Google® Android®, Microsoft® Windows Phone® OS, Microsoft® Windows Mobile® OS, Linux®, and Palm® WebOS®.

In some embodiments, a computer system 500 may be accessible through a user terminal to receive user commands. The user commands may include line commands, scripts, programs, etc., and various instructions executable by the computer system 500. A computer system 500 may receive instructions to train a neural network, search hyperparameters to train a neural network, generate a number of ligand descriptors, or schedule a computing job for the computer system 500 to carry out any instructions.

Non-Transitory Computer Readable Storage Medium

In some aspects, the present disclosure describes a non-transitory computer-readable storage media encoded with a computer program including instructions executable by one or more processors to sample a ligand using any one of the methods disclosed herein. In some embodiments, a non-transitory computer-readable storage media may comprise a neural network architecture, weights for a neural network architecture, or both. In some embodiments, a non-transitory computer-readable storage media may comprise neural network training loss history, validation loss history, test accuracies, and various measures of neural network training performance. In some embodiments, the platforms, systems, media, and methods disclosed herein include one or more non-transitory computer readable storage media encoded with a program including instructions executable by the operating system of an optionally networked computing device.

In further embodiments, a computer readable storage medium is a tangible component of a computing device. In still further embodiments, a computer readable storage medium is optionally removable from a computing device. In some embodiments, a computer readable storage medium includes, by way of non-limiting examples, flash memory devices, solid state memory, magnetic disk drives, magnetic tape drives, optical disk drives, distributed computing systems including cloud computing systems and services, and the like. In some embodiments, the program and instructions are permanently, substantially permanently, semi-permanently, or non-transitorily encoded on the media.

Computer Program

In some aspects, the present disclosure describes a computer program product comprising a computer-readable medium having computer-executable code encoded therein, the computer-executable code adapted to be executed to implement any one of the methods disclosed herein. In some embodiments, the platforms, systems, media, and methods disclosed herein include at least one computer program, or use of the same.

A computer program includes a sequence of instructions, executable by one or more processor(s) of the computing device's CPU, written to perform a specified task. Computer readable instructions may be implemented as program modules, such as functions, objects, Application Programming Interfaces (APIs), computing data structures, and the like, that perform particular tasks or implement particular abstract data types. In light of the disclosure provided herein, those of skill in the art will recognize that a computer program may be written in various versions of various languages. In some embodiments, APIs may comprise various languages, for example, languages in various releases of TensorFlow, Theano, Keras, PyTorch, or any combination thereof which may be implemented in various releases of Python, Python3, C, C#, C++, MatLab, R, Java, or any combination thereof.

The functionality of the computer readable instructions may be combined or distributed as desired in various environments. In some embodiments, a computer program comprises one sequence of instructions. In some embodiments, a computer program comprises a plurality of sequences of instructions. In some embodiments, a computer program is provided from one location. In other embodiments, a computer program is provided from a plurality of locations. In various embodiments, a computer program includes one or more software modules. In various embodiments, a computer program includes, in part or in whole, one or more web applications, one or more standalone applications, one or more web browser plug-ins, extensions, add-ins, or add-ons, or combinations thereof.

Web Application

In some embodiments, a computer program includes a web application. In some embodiments, a user may enter a query for sampling a ligand through a web application. In some embodiments, a user may add additional training data through a web application. In light of the disclosure provided herein, those of skill in the art will recognize that a web application, in various embodiments, utilizes one or more software frameworks and one or more database systems. In some embodiments, a web application is created upon a software framework such as Microsoft® .NET or Ruby on Rails (RoR). In some embodiments, a web application utilizes one or more database systems including, by way of non-limiting examples, relational, non-relational, object oriented, associative, XML, and document oriented database systems. In further embodiments, suitable relational database systems include, by way of non-limiting examples, Microsoft® SQL Server, mySQL™, and Oracle®. Those of skill in the art will also recognize that a web application, in various embodiments, is written in one or more versions of one or more languages. A web application may be written in one or more markup languages, presentation definition languages, client-side scripting languages, server-side coding languages, database query languages, or combinations thereof. In some embodiments, a web application is written to some extent in a markup language such as Hypertext Markup Language (HTML), Extensible Hypertext Markup Language (XHTML), or eXtensible Markup Language (XML). In some embodiments, a web application is written to some extent in a presentation definition language such as Cascading Style Sheets (CSS). In some embodiments, a web application is written to some extent in a client-side scripting language such as Asynchronous JavaScript and XML (AJAX), Flash® ActionScript, JavaScript, or Silverlight®. In some embodiments, a web application is written to some extent in a server-side coding language such as Active Server Pages (ASP), ColdFusion®, Perl, Java™, JavaServer Pages (JSP), Hypertext Preprocessor (PHP), Python™, Ruby, Tcl, Smalltalk, WebDNA®, or Groovy. In some embodiments, a web application is written to some extent in a database query language such as Structured Query Language (SQL). In some embodiments, a web application integrates enterprise server products such as IBM® Lotus Domino®.

Mobile Application

In some embodiments, a computer program includes a mobile application provided to a mobile computing device. In some embodiments, the mobile application is provided to a mobile computing device at the time it is manufactured. In other embodiments, the mobile application is provided to a mobile computing device via the computer network described herein.

In view of the disclosure provided herein, a mobile application is created by techniques known to those of skill in the art using hardware, languages, and development environments known to the art. Those of skill in the art will recognize that mobile applications are written in several languages. Suitable programming languages include, by way of non-limiting examples, C, C++, C#, Objective-C, Java™, JavaScript, Pascal, Object Pascal, Python™, Ruby, VB.NET, WML, and XHTML/HTML with or without CSS, or combinations thereof.

Suitable mobile application development environments are available from several sources. Commercially available development environments include, by way of non-limiting examples, AirplaySDK, alcheMo, Appcelerator®, Celsius, Bedrock, Flash Lite, .NET Compact Framework, Rhomobile, and WorkLight Mobile Platform. Other development environments are available without cost including, by way of non-limiting examples, Lazarus, MobiFlex, MoSync, and Phonegap. Also, mobile device manufacturers distribute software developer kits including, by way of non-limiting examples, iPhone and iPad (Ios) SDK, Android™ SDK, BlackBerry® SDK, BREW SDK, Palm® OS SDK, Symbian SDK, webOS SDK, and Windows® Mobile SDK.

Standalone Application

In some embodiments, a computer program includes a standalone application, which is a program that is run as an independent computer process, not an add-on to an existing process, e.g., not a plug-in. Those of skill in the art will recognize that standalone applications are often compiled. A compiler is a computer program(s) that transforms source code written in a programming language into binary object code such as assembly language or machine code. Suitable compiled programming languages include, by way of non-limiting examples, C, C++, Objective-C, COBOL, Delphi, Eiffel, Java™, Lisp, Python™, Visual Basic, and VB .NET, or combinations thereof. Compilation is often performed, at least in part, to create an executable program. In some embodiments, a computer program includes one or more executable complied applications.

Software Modules

In some embodiments, the platforms, systems, media, and methods disclosed herein include software, server, and/or database modules, or use of the same. In view of the disclosure provided herein, software modules are created by techniques known to those of skill in the art using machines, software, and languages known to the art. The software modules disclosed herein are implemented in a multitude of ways. In various embodiments, a software module comprises a file, a section of code, a programming object, a programming structure, a distributed computing resource, a cloud computing resource, or combinations thereof. In further various embodiments, a software module comprises a plurality of files, a plurality of sections of code, a plurality of programming objects, a plurality of programming structures, a plurality of distributed computing resources, a plurality of cloud computing resources, or combinations thereof. In various embodiments, the one or more software modules comprise, by way of non-limiting examples, a web application, a mobile application, a standalone application, and a distributed or cloud computing application. In some embodiments, software modules are in one computer program or application. In other embodiments, software modules are in more than one computer program or application. In some embodiments, software modules are hosted on one machine. In other embodiments, software modules are hosted on more than one machine. In further embodiments, software modules are hosted on a distributed computing platform such as a cloud computing platform. In some embodiments, software modules are hosted on one or more machines in one location. In other embodiments, software modules are hosted on one or more machines in more than one location.

Databases

In some embodiments, the platforms, systems, media, and methods disclosed herein include one or more databases, or use of the same. In view of the disclosure provided herein, those of skill in the art will recognize that many databases are suitable for storage and retrieval of information about chemical datasets, latent descriptors, or any combination thereof. In various embodiments, suitable databases include, by way of non-limiting examples, relational databases, non-relational databases, object oriented databases, object databases, entity-relationship model databases, associative databases, XML databases, document oriented databases, and graph databases. Further non-limiting examples include SQL, PostgreSQL, MySQL, Oracle, DB2, Sybase, and MongoDB. In some embodiments, a database is Internet-based. In further embodiments, a database is web-based. In still further embodiments, a database is cloud computing-based. In a particular embodiment, a database is a distributed database. In other embodiments, a database is based on one or more local computer storage devices.

EXAMPLES

The following examples are provided to further illustrate some embodiments of the present disclosure, but are not intended to limit the scope of the disclosure; it will be understood by their exemplary nature that other procedures, methodologies, or techniques known to those skilled in the art may alternatively be used.

Example 1: Model Training

Data

The model was trained with the scPDB and Biolip dataset. The two datasets are comprised of 16034 and 445803 protein-ligand pairs, respectively. The protein-ligand pairs are crystal structures in the datasets. The datasets were first filtered for compounds with Glucose-Tri-Phosphate/Glucose-Di-Phosphate or natural products. Structures having resolution larger than 3.5 Å are removed. This resulted in 8294 and 17615 protein-ligand pairs in scPDB and Biolip, respectively. Protein-ligand pairs in scPDB were randomly split into a training set and a test set with sizes 7000 and 1294, respectively. Protein-ligand pairs in Biolip were split into a training set and a test set with sizes 14000 and 3615, respectively.

Data Featurization

The data was featurized using the protein-ligand interaction profiler tool ("plip", Adasme et al. PUP 2021: expanding the scope of the protein-ligand interaction profiler to DNA and RNA. NAR 2021) to annotate interacting atoms. Python package HTMD was used to voxelate the data into a discretized cubic grid. A crystal structure of a protein-ligand pair was transformed to a four-dimensional (Height× Width×Length×Channels) tensors, which is illustrated in FIG. 1. Each channel, of a total of 13 channels in the data, represents one or more pharmacophore properties, one or more interaction labels for atoms or heavy atoms (occupancy), and one or more labels for atoms. Channels 1 to 13 correspondingly represents 'hydrophobic', 'aromatic', 'hbond_acceptor', 'hbond_donor', 'positive_ionizable', 'negative_ionizable', 'metal', 'pocket occupancies', 'residue hbond interaction', 'residue hydrophobic interaction', 'residue pi-pi interaction', 'residue halogen interaction', and 'ligand occupancies'.

The goal of the training is to create a model that can be given an empty pocket (input), and generate a good molecule to fit in this pocket. By following the data featurization steps, the protein-ligand complex PDB files are transformed into 32×32×32×13 voxelated 4D tensors, each paired with corresponding SMILES of ligands. The first 12 channels of the 4D tensor are taken as the input of the model. The last channel of the 4D tensor, which is the ligand occupancy, is used as the output of the model. The SMILES of the ligands are also used as outputs. The SMILES of the ligand were used to generate Morgan fingerprints for each SMILES in the dataset.

Model Architecture

Figure 2:
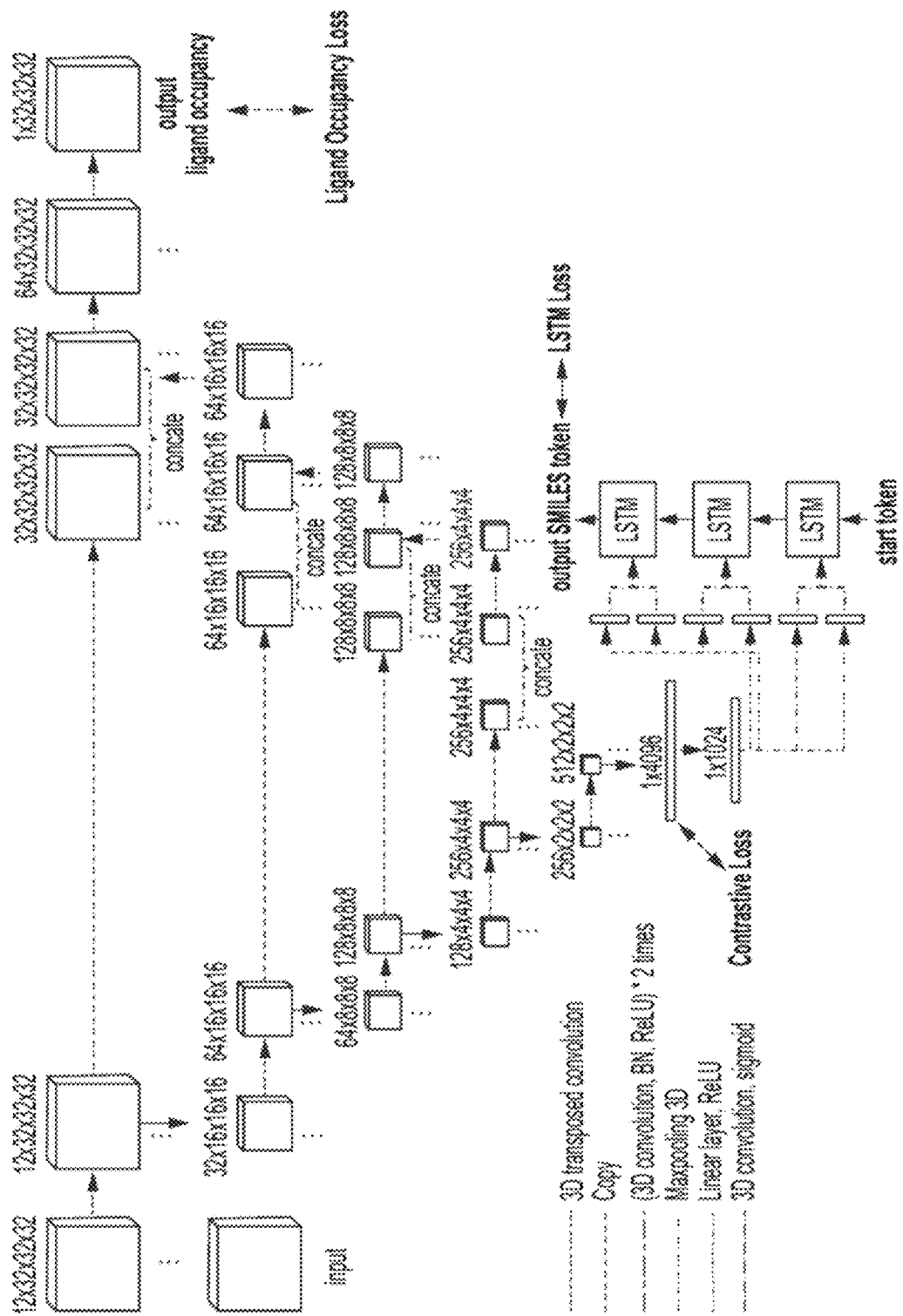
FIG. 2 schematically illustrates a neural network architecture, in accordance with some embodiments. The neural network comprises a U-Net and a LSTM. Output from the bottleneck layer of the U-Net (latent descriptor) is passed through 6 linear dense layers to serve as initial memory nodes for the language model (e.g., LSTM) to steer SMILES generation towards ligands with structure and/or properties that fit the input pocket. The neural network architecture allows learning two tasks together, for example, both (i) outputting ligand occupancy from U-Net decoder and (ii) SMILES from LSTM, to create more efficient latent embeddings.
Figure 3:
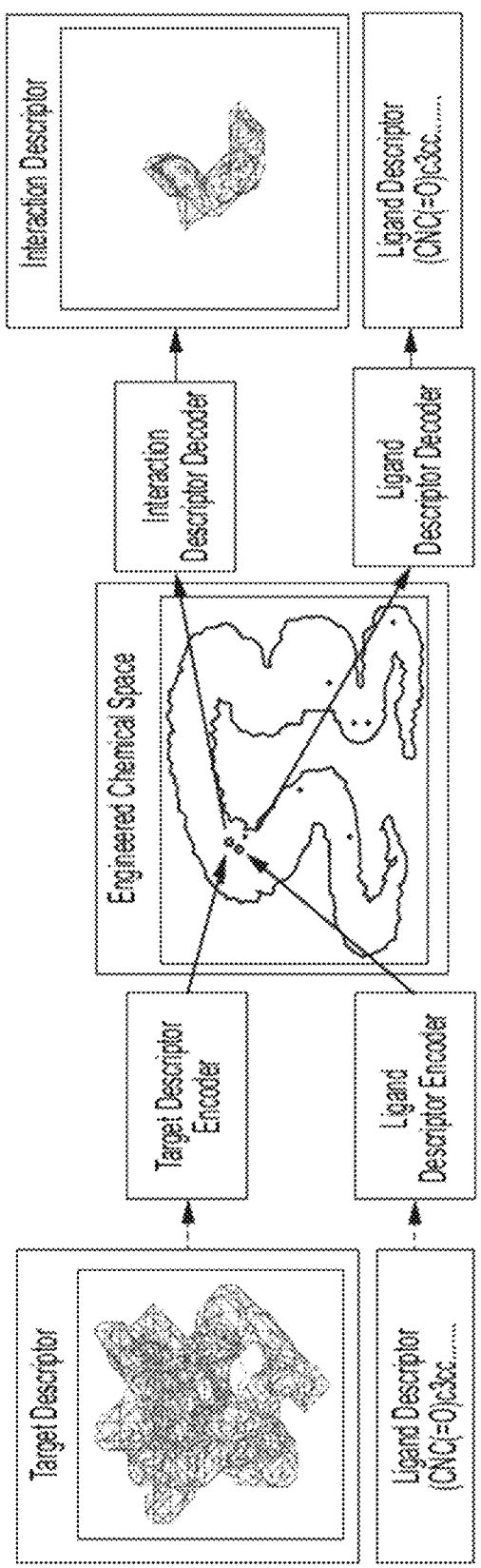
FIG. 3 illustrates some concepts underlying contrastive learning, in accordance with some embodiments. Two encoders may be used to learn a joint embedding (e.g., in a multimodal space) for 'image' and 'string' pairs. A decoder may be used to interpret latent descriptors from the joint embedding space, while incorporating a new 'image', to generate new content. For example, an encoder may be used to create a latent descriptor from an image, and a decoder may be used to generate a string (e.g., a descriptive sentence) describing the image. For another example, an encoder may be used to create a latent descriptor from a string (e.g., a sentence), and a decoder may be used to generate an image based on the string.

FIG. 2 illustrates the overall architecture of the model. The architecture can be divided into two parts, U-Net and LSTM model. Information flows from the input of the U-Net which receives an empty pocket tensor (e.g., the featurized data without the ligand occupancy channel), and to the output the U-Net which outputs a ligand occupancy tensor and to the output of the LSTM which outputs SMILES of the ligand occupying the empty pocket. The model is a multi-task learning model (outputting ligand occupancy and ligand SMILES). By learning the two tasks together, spatial information from the U-net architecture (learned through inputting tensors of empty pocket and outputting tensors of ligand occupancy) can be shared with the LSTM's memory, through the bottleneck layer.

The encoder in the U-Net starts with 4 residual blocks. Each residual block consists of 2 3×3×3 convolutional layers, 2 batch normalization layers, and 2 ReLU. A max pooling operation is applied after each residual block.

After feeding the 12×32×32×32 4D tensor input into the encoder, the target latent descriptor is obtained, which is a lower dimensional representation of the information from the empty pocket. The target latent descriptor extracted by the encoder is transformed by the 6 dense linear layers as the initial memory state of the LSTM, steering the language model to generate the SMILES of molecules that fit the pocket.

The pocket descriptor is decoded using 3D transpose convolutions, concatenation with corresponding feature maps from the contracting paths, and passing through the residual blocks mentioned in the encoder. After 3 repetitions, the last layer, a convolution layer followed by a sigmoid activation function, is used to map the 4D tensor to the output 3D tensor, the ligand occupancy.

LSTM

In parallel with the existing U-Net architecture, one more branch, LSTM, is added to predict the ligand SMILES that occupies the input pocket. The target latent descriptor extracted by the encoder is passed through 6 linear layers as the initial cell and hidden states in the LSTM. Therefore, the LSTM incorporates the pocket information to generate SMILES of ligands that fit the input pocket.

Loss Function

The model is trained using a combination of loss functions.

Ligand Occupancy Loss $$L(X_o, Y_o) = \|X_o - Y_o\|_2^2$$

wherein $L(X_o, Y_o)$ denotes the first reconstruction loss,
wherein $X_o$ is a ligand occupancy descriptor in the training data,
wherein $Y_o$ is a reconstruction of the ligand occupancy descriptor by the bottleneck architecture, and
$\|x\|_p \equiv (x_1^p + \ldots + x_n^p)^{1/p}$.

LSTM Loss $$L(X_f, Y_f) = -\Sigma_i^n Y_{f,i} \cdot \log(X_{f,i})$$

wherein $L(X_f, Y_f)$ denotes the second reconstruction loss,
wherein $-\Sigma_i^n$ denotes a negative summation over each element i of in a total of n elements in the operands,
wherein $X_{f,i}$ is a ligand identifier element in the training data, and
wherein $Y_{f,i}$ is a ligand identifier element that is reconstructed by the language model.

Contrastive Loss $$L(p,f) = [a - \text{sim}(p,f) + \text{sim}(p,f')]_+ + [a - \text{sim}(p,f) + \text{sim}(p',f)]_+$$

wherein $L(p,f)$ denotes the contrastive loss,
a is a margin parameter,
p is a first target descriptor in a training data,
f is a first ligand descriptor in the training data,
p' is a second target descriptor in the training data that is least similar to the first ligand descriptor,
f' is a second ligand descriptor in the training data that is least similar to the first target descriptor,
sim is a similarity function computed between its parentheticals, and
$[x]_+ = \max(x, 0)$.

The ligand occupancy loss leads the model to extract information from the input pocket and generate the ligand spatial information (ligand occupancy) accordingly.

The contrastive loss embeds the target latent descriptor from the empty pocket and the fingerprint of the crystal ligand (e.g., Morgan Fingerprints) into the same embedding space. Through this loss, the target latent descriptors extracted from the encoder are more connected to the ligand latent descriptors (e.g., Morgan Fingerprints), which makes the language model utilize the pocket information more.

Example 2: Model Inference

This example describes systems and methods generating a ligand descriptor and/or an interaction descriptor, in accordance with some embodiments. FIG. 4, top panel shows an inference method that receives a target descriptor of a target as input, and outputs ligand occupancy of the target and/or a ligand identifier for a candidate ligand that is predicted to bind with the target.

The target descriptor may be a spatial map of a protein pocket. A target descriptor encoder transforms the target descriptor into a latent descriptor in the engineered chemical space. Then, the ligand descriptor decoder transforms the latent descriptor into a ligand descriptor. This mode of inference can be useful, for instance, when generating candidate drugs for targeting a protein target. By providing a description of a protein target, an identifier of a candidate drug may be generated.

Alternatively, or in conjunction, a target descriptor decoder transforms the latent descriptor into an interaction descriptor. This mode of inference can be useful, for instance, when studying how a protein target may interact with a candidate drug. By providing a description of a protein target, a prediction of how a target and ligand can interact may be generated.

FIG. 4, middle panel shows an inference method that receives a target descriptor of a target as input to output a latent descriptor in the engineered chemical space, which may be navigated (e.g., by adding noise) to select a different latent descriptor, and outputs a candidate ligand that is predicted to bind with the target. This illustrates that once a latent descriptor has been generated from a target descriptor, another latent descriptor may be chosen automatically (e.g., adding random noise to the latent descriptor) or purposefully by a human being (e.g., a human expert navigates the engineered chemical space to explore other possible latent descriptors). The latent descriptor, once chosen, can be decoded to yield a ligand descriptor.

FIG. 4, bottom panel shows an inference method that receives a ligand identifier as input to output a latent descriptor in the engineered chemical space, which may be navigated to select a different latent descriptor, and outputs a new candidate ligand that may target similar targets as the ligand of the input ligand descriptor. In some embodiments, the engineered chemical space may have organized latent descriptors such that the proximal latent descriptors map to ligands that target similar targets.

Numbered Embodiments

The following list of numbered embodiments of the invention are to be considered as disclosing various features of the invention, which features can be considered to be specific to the particular embodiment under which they are discussed, or which are combinable with the various other features as listed in other embodiments. Thus, simply because a feature is discussed under one particular embodiment does not necessarily limit the use of that feature to that embodiment.

Embodiment 1. A method of sampling a ligand, comprising: (a) receiving a target descriptor; (b) generating, in an engineered chemical space, a latent descriptor, based at least in part on the target descriptor; and (c) generating a ligand descriptor, based at least in part on the latent descriptor.

Embodiment 2. The method of embodiment 1, wherein the engineered chemical space comprises a unified embedding for at least a plurality of target latent descriptors and a plurality of ligand latent descriptors.

Embodiment 3. The method of embodiment 1 or 2, wherein, in the engineered chemical space, a given target latent descriptor of a given target has a similarity with a given ligand latent descriptor of a given ligand when the given ligand targets the given target, and has a dissimilarity when the given ligand does not target the given target.

Embodiment 4. The method of embodiment 3, wherein the given target latent descriptor is not identical to the given ligand latent descriptor.

Embodiment 5. The method of any one of embodiments 1-4, wherein the engineered chemical space is at least partially organized based on spatial information of a plurality of ligands, a plurality of targets, or both.

Embodiment 6. The method of any one of embodiments 3-5, wherein the similarity or the dissimilarity is measurable using a similarity function.

Embodiment 7. The method of embodiment 6, wherein the similarity function comprises a distance-based similarity function, an angle-based similarity function, a set-based similarity function, or any combination thereof.

Embodiment 8. The method of embodiment 7, wherein the angle-based similarity function is a cosine similarity function.

Embodiment 9. The method of any one of embodiments 1-8, wherein the method is performed at least in part by using a neural network.

Embodiment 10. The method of embodiment 9, wherein the generating in (b) is performed at least in part by using an encoder.

Embodiment 11. The method of embodiment 9 or 10, wherein the generating in (c) is performed at least in part by using a decoder.

Embodiment 12. The method of embodiment 11, wherein the neural network comprises a bottleneck architecture comprising the encoder and the decoder.

Embodiment 13. The method of embodiment 12, wherein the bottleneck architecture comprises a U-net.

Embodiment 14. The method of any one of embodiments 11-13, wherein the decoder comprises a language model.

Embodiment 15. The method of embodiment 14, wherein the language model is a long-short-term-memory model (LSTM).

Embodiment 16. The method of embodiment 15, wherein at least one hidden unit of the LSTM is initialized with the latent descriptor.

Embodiment 17. The method of any one of embodiments 9-16, wherein the neural network comprises a convolutional layer.

Embodiment 18. The method of any one of embodiments 9-17, wherein the neural network comprises a densely-connected layer.

Embodiment 19. The method of any one of embodiments 9-18, wherein the neural network comprises a skip connection.

Embodiment 20. The method of any one of embodiments 10-19, wherein the generating the latent descriptor is performed using at least the encoder.

Embodiment 21. The method of any one of embodiments 10-20, wherein at least the encoder is trained at least in part by using contrastive learning.

Embodiment 22. The method of embodiment 21, wherein the contrastive learning is based at least in part on a contrastive loss computed between pairs formed between the target latent descriptors and the ligand latent descriptors from a training data.

Embodiment 23. The method of embodiment 22, wherein the contrastive loss comprises at least:

$$L(p,f)=[a-\text{sim}(p,f)+\text{sim}(p,f')]_+ + [a-\text{sim}(p,f)+\text{sim}(p',f)]_+$$

wherein L(p,f) denotes the contrastive loss,
a is a margin parameter,
p is a first target latent descriptor from the training data,
f is a first ligand latent descriptor from the training data,
p' is a second target latent descriptor from the training data that is least similar to the first ligand latent descriptor,
f' is a second ligand latent descriptor from the training data that is least similar to the first target latent descriptor,
sim is a similarity function computed between its parentheticals, and
$[x]_+ \equiv \max(x,0)$.

Embodiment 24. The method of any one of embodiments 1-23, wherein the generating the ligand descriptor is performed stochastically.

Embodiment 25. The method of embodiment 24, wherein the language model is trained based at least in part on a first reconstruction loss.

Embodiment 26. The method of embodiment 25, wherein the first reconstruction loss is a probabilistic loss function.

Embodiment 27. The method of embodiment 26, wherein the first reconstruction loss comprises at least:

$$L(X_f, Y_f) = -\Sigma_i^n Y_{f,i} \cdot \log(X_{f,i})$$

wherein $L(X_f, Y_f)$ denotes the first reconstruction loss,
wherein $-\Sigma_i^n$ denotes a negative summation over each element i of in a total of n elements in the operands,
wherein $X_{f,i}$ is a ligand identifier element from the training data, and
wherein $Y_{f,i}$ is a ligand identifier element that is reconstructed by the language model.

Embodiment 28. The method of any one of embodiments 1-27, wherein the ligand descriptor comprises a ligand identifier.

Embodiment 29. The method of embodiment 28, wherein the ligand identifier comprises a textual identifier.

Embodiment 30. The method of embodiment 29, wherein the textual identifier comprises SMILES, InChI, or SELFIES.

Embodiment 31. The method of embodiment 28 or 29, wherein the ligand identifier comprises a molecular adjacency matrix or a molecular graph.

Embodiment 32. The method of any one of embodiments 12-31, wherein the bottleneck architecture is trained at least in part on a second reconstruction loss based at least in part on a target-ligand interaction.

Embodiment 33. The method of embodiment 32, wherein the target-ligand interaction comprises ligand occupancy.

Embodiment 34. The method of embodiment 33, wherein the second reconstruction loss comprises at least:

$$L(X_o, Y_o) = \|X_o - Y_o\|_2^2$$

wherein $L(X_o, Y_o)$ denotes the second reconstruction loss,
wherein $X_o$ is a ligand occupancy descriptor in the training data, and
wherein $Y_o$ is a reconstruction of the ligand occupancy descriptor by the autoencoder.

Embodiment 35. The method of any one of embodiments 1-34, wherein the target descriptor comprises a protein target descriptor.

Embodiment 36. The method of any one of embodiments 1-35, wherein the target descriptor comprises a protein pocket descriptor.

Embodiment 37. The method of any one of embodiments 1-36, wherein the target descriptor comprises features that describe at least one of: hydrophobicity, aromaticity, hydrogen bond accepting, hydrogen bond donating, positive ionizability, negative ionizability, metallicity, pocket occupancy, hydrogen bond interaction ability, hydrophobic interaction ability, pi-pi interaction ability, and halogen interaction ability.

Embodiment 38. The method of embodiment 36 or 37, wherein the protein pocket descriptor comprises a spatial map of one or more protein targets.

Embodiment 39. The method of embodiment 38, wherein the spatial map is a grid.

Embodiment 40. The method of embodiment 39, wherein the spatial map is a rectangular grid.

Embodiment 41. The method of embodiment 40, wherein the spatial map comprises at least 3 dimensions.

Embodiment 42. The method of embodiment 41, wherein the spatial map comprises a resolution less than about 3.5 Angstroms.

Embodiment 43. A computer-implemented method, implementing any one of the methods of embodiments 1-42 in a computer.

Embodiment 44. A computer program product comprising a computer-readable medium having computer-executable code encoded therein, the computer-executable code adapted to be executed to implement any one of the methods of embodiments 1-42.

Embodiment 45. A non-transitory computer-readable storage media encoded with a computer program including instructions executable by one or more processors to sample a ligand using any one of the methods of embodiments 1-42.

Embodiment 46. A computer-implemented system comprising: a digital processing device comprising: at least one processor, an operating system configured to perform executable instructions, a memory, and a computer program including instructions executable by the digital processing device to sample a ligand using any one of the methods of embodiments 1-42.

Embodiment 47. A method of machine learning an engineered chemical space, comprising: (a) providing a neural network comprising: i. an input layer configured to receive at least a target descriptor; ii. a latent layer configured to output at least a latent descriptor, wherein the latent layer is connected to the input layer; iii. an output layer configured to output at least a target-ligand interaction descriptor, wherein the output layer is connected to the latent layer; iv. at least one parameter; (b) providing training data comprising a plurality of target descriptors, a plurality of target-ligand interaction descriptors, and a plurality of ligand latent descriptors; (c) training the neural network, by (i) inputting at least the plurality of target descriptors at the input layer of the neural network, (ii) outputting a plurality of output latent descriptors at the latent layer and a plurality of output target-ligand interaction descriptors at the output layer, and (iii) optimizing a plurality of loss functions based at least in part on the plurality of output latent descriptors and the plurality of output target-ligand interaction descriptors, by updating the at least one parameter of the neural network, such that the neural network learns the engineered chemical space comprising a unified embedding for at least the plurality of target descriptors and the plurality of ligand latent descriptors.

Embodiment 48. The method of embodiment 47, wherein the engineered chemical space is at least partially organized based on spatial information of the plurality of target descriptors and the plurality of ligand latent descriptors.

Embodiment 49. The method of embodiment 47 or 48, wherein, in the engineered chemical space, a given target latent descriptor of a given target has a similarity with a given ligand latent descriptor of a given ligand when the given ligand targets the given target, and has a dissimilarity when the given ligand does not target the given target.

Embodiment 50. The method of embodiment 49, wherein the given target latent descriptor is not identical to the given ligand latent descriptor.

Embodiment 51. The method of embodiment 49 or 50, wherein the similarity or the dissimilarity is measurable using a similarity function.

Embodiment 52. The method of any one of embodiments 47-51, wherein the plurality of loss functions comprises a contrastive loss function computed between a plurality of pairs formed between a plurality of target latent descriptors output by the latent layer and a plurality ligand latent descriptors.

Embodiment 53. The method of any one of embodiments 47-52, wherein the training the neural network comprises optimizing a loss function comprising a first reconstruction loss function computed between the plurality of target-ligand interaction descriptors of the training data and a plurality of reconstructed target-ligand interaction descriptors output by the first output layer.

Embodiment 54. The method of any one of embodiments 47-53, wherein the neural network further comprises a second output layer configured to output at least a ligand descriptor, wherein the second output layer is connected to the latent layer.

Embodiment 55. The method of any one of embodiments 47-54, wherein the training data further comprises a plurality of ligand descriptors.

Embodiment 56. The method of any one of embodiments 47-55, wherein the training the neural network further comprises outputting a plurality of output ligand descriptors, and optimizing a loss function comprising a second reconstruction loss function computed between the plurality of ligand descriptors of the training data and a plurality of output target-ligand interaction descriptors output by the second output layer.

Embodiment 57. The method of any one of embodiments 47-56, wherein the plurality of target descriptors of the training data comprises features that describe at least one of: hydrophobicity, aromaticity, hydrogen bond accepting, hydrogen bond donating, positive ionizability, negative ionizability, metallicity, pocket occupancy, hydrogen bond interaction ability, hydrophobic interaction ability, pi-pi interaction ability, and halogen interaction ability.

Embodiment 58. The method of any one of embodiments 47-57, wherein the plurality of target-ligand interaction descriptors in the training data comprises ligand occupancy of a given target.

Embodiment 59. The method of any one of embodiments 47-58, wherein the plurality of ligand latent descriptors in the training data comprises SMILES of a given ligand.

Embodiment 60. The method of any one of embodiments 47-59, wherein the neural network further comprises a plurality of hidden layers connecting at least two of: the input layer, the latent layer, and first output layer, and the second output layer.

Embodiment 61. A computer-implemented method, implementing any one of the methods of embodiments 47-60 in a computer.

Embodiment 62. A computer program product comprising a computer-readable medium having computer-executable code encoded therein, the computer-executable code adapted to be executed to implement any one of the methods of embodiments 47-60.

Embodiment 63. A non-transitory computer-readable storage media encoded with a computer program including instructions executable by one or more processors to train a neural network using any one of the methods of embodiments 47-60.

Embodiment 64. A computer-implemented system comprising: a digital processing device comprising: at least one processor, an operating system configured to perform executable instructions, a memory, and a computer program including instructions executable by the digital processing device to train a neural network using any one of the methods of embodiments 47-60.

While preferred embodiments of the present disclosure have been shown and described herein, it will be obvious to those skilled in the art that such embodiments are provided by way of example only. Numerous variations, changes, and substitutions will now occur to those skilled in the art without departing from the disclosure. It should be understood that various alternatives to the embodiments of the present disclosure may be employed in practicing the present disclosure. It is intended that the following claims define the scope of the present disclosure and that methods and structures within the scope of these claims and their equivalents be covered thereby.

What is claimed is:

1. A computer-implemented method of generating a candidate ligand that is predicted to bind with a target, comprising:
    (a) receiving a target descriptor representing the target;
    (b) generating, in an engineered chemical space, a latent descriptor of the candidate ligand using a neural network, wherein the generating is performed based at least in part on processing the target descriptor using the neural network, wherein the neural network is trained to incorporate at least two sources of chemical information into the engineered chemical space, and wherein the at least two sources of chemical information comprise (i) a plurality of target structures of a plurality of targets and (ii) a plurality of ligand structures of a plurality of ligands that bind to the plurality of targets; and
    (c) generating a ligand descriptor of the candidate ligand, based at least in part on processing the latent descriptor using the neural network;
    wherein the engineered chemical space comprises a unified embedding for the at least two sources of chemical information, wherein the unified embedding comprises (i) a plurality of target latent descriptors for the plurality of targets and (ii) a plurality of ligand latent descriptors for the plurality of ligands,
    wherein the generating in (b) is performed at least in part by using an encoder, and wherein the generating in (c) is performed at least in part by using a decoder, and wherein the neural network comprises a bottleneck architecture comprising the encoder and the decoder, and
    wherein at least the encoder is trained at least in part by using contrastive learning, wherein the contrastive learning is based at least in part on a contrastive loss computed between pairs formed between the target latent descriptors and the ligand latent descriptors from a training data, and wherein the contrastive loss comprises at least:

$$L(p,f)=[a-\operatorname{sim}(p,f)+\operatorname{sim}(p,f')]_{+}+[a-\operatorname{sim}(p,f)+\operatorname{sim}(p',f)]_{+}$$

wherein L(p,f) denotes the contrastive loss,
a is a margin parameter,
p is a first target latent descriptor in a training data,
f is a first ligand latent descriptor in the training data,
p' is a second target latent descriptor in the training data that is least similar to the first ligand latent descriptor,
f' is a second ligand latent descriptor from the training data that is least similar to the first target latent descriptor,
sim is a similarity function computed between its parentheticals, and
$[x]_{+}$max(x,0).

2. The computer-implemented method of claim 1, wherein the bottleneck architecture comprises a U-net.

3. The computer-implemented method of claim 1, wherein the decoder comprises a language model.

4. The computer-implemented method of claim 1, wherein the decoder is trained based at least in part on a first reconstruction loss comprising at least:

$$L(X_f, Y_f) = -\Sigma_i^n Y_{f,i} \cdot \log(X_{f,i})$$

wherein $L(X_f, Y_f)$ denotes the first reconstruction loss,
wherein $-\Sigma_i^n$ denotes a negative summation over each element i of in a total of n elements,
wherein $X_{f,i}$ is a ligand identifier element in the training data, and
wherein $Y_{f,i}$ is a ligand identifier element that is reconstructed by the decoder.

5. The computer-implemented method of claim 1, wherein the bottleneck architecture is trained at least in part on a second reconstruction loss based at least in part on a target-ligand interaction.

6. The computer-implemented method of claim 5, wherein the target-ligand interaction is ligand occupancy.

7. The computer-implemented method of claim 1, wherein the target descriptor comprises a protein pocket descriptor.

8. The computer-implemented method of claim 1, wherein the encoder comprises (i) a first encoder that encodes the plurality of target structures of a-the plurality of targets into the engineered chemical space, and (ii) a second encoder that encodes the plurality of ligand structures of the plurality of ligands that bind to the plurality of targets into the engineered chemical space.

9. A computer-implemented method of generating a candidate ligand that is predicted to bind with a target, comprising:
(a) receiving a target descriptor representing the target;
(b) generating, in an engineered chemical space, a latent descriptor of the candidate ligand using a neural network, wherein the generating is performed based at least in part on processing the target descriptor using the neural network, wherein the neural network is trained to incorporate at least two sources of chemical information into the engineered chemical space, and wherein the at least two sources of chemical information comprise (i) a plurality of target structures of a plurality of targets and (ii) a plurality of ligand structures of a plurality of ligands that bind to the plurality of targets; and (c) generating a ligand descriptor of the candidate ligand, based at least in part on processing the latent descriptor using the neural network;
wherein, in the engineered chemical space, (i) a first target latent descriptor of a first target in the plurality of targets has a higher similarity measure with a ligand latent descriptor of a ligand in the plurality of ligands when the ligand targets the first target, and (ii) a second target latent descriptor of a second target in the plurality of targets has a lower similarity measure with the ligand latent descriptor when the ligand does not target the second target, wherein the similarity measure is based on a similarity function,
wherein the generating in (b) is performed at least in part by using an encoder, and wherein the generating in (c) is performed at least in part by using a decoder, and wherein the neural network comprises a bottleneck architecture comprising the encoder and the decoder, and
wherein at least the encoder is trained at least in part by using contrastive learning, wherein
the contrastive learning is based at least in part on a contrastive loss computed between pairs formed between the target latent descriptors and the ligand latent descriptors from a training data, and wherein the contrastive loss comprises at least:

$$L(p,f)=[a-\operatorname{sim}(p,f)+\operatorname{sim}(p,f')]_{+}+[a-\operatorname{sim}(p,f)+\operatorname{sim}(p',f)]_{+}$$

wherein L(p,f) denotes the contrastive loss,
a is a margin parameter,
p is a first target latent descriptor in a training data,
f is a first ligand latent descriptor in the training data,
p' is a second target latent descriptor in the training data that is least similar to the first ligand latent descriptor,
f' is a second ligand latent descriptor from the training data that is least similar to the first target latent descriptor,
sim is a similarity function computed between its parentheticals, and
$[x]_{+}$max(x,0).

10. The computer-implemented method of claim 9, wherein the first target latent descriptor is not identical to the ligand latent descriptor.

11. The computer-implemented method of claim 9, wherein the target descriptor comprises a protein pocket descriptor.

12. The computer-implemented method of claim 11, wherein the protein pocket descriptor comprises a spatial map of one or more protein targets.

13. The computer-implemented method of claim 9, wherein the neural network comprises a U-net.

14. The computer-implemented method of claim 9, wherein the neural network comprises a language model.

15. The computer-implemented method of claim 9, wherein the encoder comprises (i) a first encoder that encodes the plurality of target structures of a-the plurality of targets into the engineered chemical space, and (ii) a second encoder that encodes the plurality of ligand structures of the plurality of ligands that bind to the plurality of targets into the engineered chemical space.

16. A computer-implemented method of generating a candidate ligand that is predicted to bind with a target, comprising:
(a) receiving a target descriptor representing the target;
(b) generating, in an engineered chemical space, a latent descriptor of the candidate ligand using a neural network, wherein the generating is performed based at least in part on processing the target descriptor using the neural network, wherein the neural network is trained to incorporate at least two sources of chemical information into the engineered chemical space, and wherein the at least two sources of chemical information comprise (i) a plurality of target structures of a plurality of targets and (ii) a plurality of ligand structures of a plurality of ligands that bind to the plurality of targets; and (c) generating a ligand descriptor of the candidate ligand, based at least in part on processing the latent descriptor using the neural network;

wherein the engineered chemical space is at least partially organized based on spatial information of the plurality of ligands and the plurality of targets, wherein the generating in (b) is performed at least in part by using an encoder, and wherein the generating in (c) is performed at least in part by using a decoder, and wherein the neural network comprises a bottleneck architecture comprising the encoder and the decoder, and wherein at least the encoder is trained at least in part by using contrastive learning, wherein the contrastive learning is based at least in part on a contrastive loss computed between pairs formed between the target latent descriptors and the ligand latent descriptors from a training data, and wherein the contrastive loss comprises at least:

$$L(p,f)=[a-\text{sim}(p,f)+\text{sim}(p,f')]_{+}+[a-\text{sim}(p,f)+\text{sim}(p',f)]_{+}$$

wherein $L(p,f)$ denotes the contrastive loss, a is a margin parameter, p is a first target latent descriptor in a training data, f is a first ligand latent descriptor in the training data, p' is a second target latent descriptor in the training data that is least similar to the first ligand latent descriptor, f' is a second ligand latent descriptor from the training data that is least similar to the first target latent descriptor, sim is a similarity function computed between its parentheticals, and $[x]_{+}\text{max}(x,0)$.

17. The computer-implemented method of claim 16, wherein the target descriptor comprises a protein pocket descriptor.

18. The computer-implemented method of claim 17, wherein the protein pocket descriptor comprises a spatial map of one or more protein targets.

19. The computer-implemented method of claim 16, wherein the neural network comprises a U-net.

20. The computer-implemented method of claim 16, wherein the neural network comprises a language model.

21. The computer-implemented method of claim 16, wherein the spatial information of the plurality of ligands comprises a plurality of ligand occupancies.

22. The computer-implemented method of claim 16, wherein the encoder comprises (i) a first encoder that encodes the plurality of target structures of thea plurality of targets into the engineered chemical space, and (ii) a second encoder that encodes the plurality of ligand structures of the plurality of ligands that bind to the plurality of targets into the engineered chemical space.

* * * * *